United States Patent
Brenner et al.

(10) Patent No.: US 6,255,327 B1
(45) Date of Patent: Jul. 3, 2001

(54) DIPHENYL-SUBSTITUTED HETEROCYCLES, PROCESSES FOR PREPARING THEM AND THEIR USE AS PHARMACEUTICAL COMPOSITIONS

(75) Inventors: Michael Brenner, Bingen; Wolf-Dietrich Bechtel, Appenheim; Rainer Palluk, Bingen; Marion Wienrich, Weiterstadt; Thomas Weiser, Nieder-Olm, all of (DE); Enzo Cereda, Novi Ligure (IT); Maura Bignotti, Milan (IT); Carlo Maria Pellegrini, Casalpusterlengo (IT)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/290,931

(22) Filed: Apr. 13, 1999

(30) Foreign Application Priority Data

Feb. 1, 1998 (IT) .............................. MI98A0818
Apr. 17, 1998 (DE) .............................. 198 16 880

(51) Int. Cl.$^7$ ........................ C07D 271/06; A61K 31/421
(52) U.S. Cl. ........................ 514/364; 514/374; 514/378; 514/383; 514/392; 514/400; 514/403; 514/427; 548/144; 548/235; 548/247; 548/267.2; 548/320; 548/340.1; 548/375.1; 548/561

(58) Field of Search ............................ 548/561, 144, 548/235, 267.2, 320.1, 340.1, 375.1, 247; 514/383, 374, 364, 392, 400, 403, 427, 378

(56) References Cited

FOREIGN PATENT DOCUMENTS

1356901 * 2/1964 (FR) .............................. 548/561
WO 98/17652 4/1998 (WO) .

* cited by examiner

Primary Examiner—Robert Gerstl
(74) Attorney, Agent, or Firm—Robert P. Raymond; Alan R. Stempel; Mary-Ellen M. Devlin

(57) ABSTRACT

The invention relates to new diphenyl-substituted 5-ring heterocycles of general formula (I)

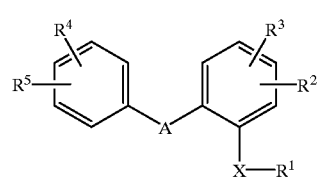

wherein A, X and the groups $R^1$, $R^2$, $R^3$, $R^4$ and $R^5$ are defined as in the claims, processes for preparing them and their use as pharmaceutical compositions.

4 Claims, No Drawings

DIPHENYL-SUBSTITUTED HETEROCYCLES, PROCESSES FOR PREPARING THEM AND THEIR USE AS PHARMACEUTICAL COMPOSITIONS

The invention relates to new diphenyl-substituted 5-ring heterocycles, processes for preparing them and their use as pharmaceutical compositions.

The new compounds have the structure of general formula (I)

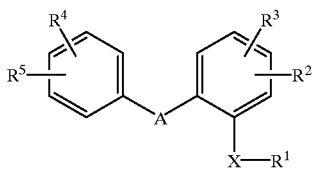

wherein
- A denotes a 5-membered saturated or unsaturated heterocycle other than 1,2,4-oxadiazole, which may contain 1, 2 or 3 heteroatoms selected from the group comprising oxygen, nitrogen or sulphur and is optionally mono- or polysubstituted by $-OR^8$, $=O$ or $C_1-C_6$-alkyl, whilst the $C_1-C_6$-alkyl group may in turn be substituted by halogen, hydroxy or $-NR^6R^7$;
- X denotes oxygen, sulphur or $NR^6$;
- $R^1$ denotes a $C_1-C_{10}$-alkyl, $C_2-C_{10}$-alkenyl or $C_2-C_{10}$-alkynyl group which may optionally be mono- or polysubstituted by $=O$, $-CN$, $-CHO$, $C_6-C_{10}$-aryl, $-COOR^8$, $-CONHSO_2R^8$, $-CONR^6R^7$, $-CH=NOR^8$, $-COR^8$, $-NR^6R^7$, $-NHCOR^8$, $-NHCONR^6R^7$, $-NHCOOR^8$, $-OR^8$, $-OCOR^8$, $-OCOOR^8$, $-OCONR^6R^7$, $-SR8$, $-SOR^8$, $-SO_2R8$, $-SO_3H$, $-SO_2NR^6R^7$, halogen or by an N-oxide of the formula $-NOR^6R^7$;
- $R^2$ and $R^3$, which may be identical or different, denote hydrogen, mercapto, $-NR^6R^7$, halogen, nitro, $CF_3$, CN, $-OR^8$, $C_1-C_{10}$-alkyl, $C_2-C_{10}$-alkenyl or $C_2-C_{10}$-alkynyl,
- $R^2$ and $R^3$ denote $C_6-C_{10}$-aryl, aryl-$C_1-C_6$-alkyl, $C_6-C_{10}$-aryloxy;
- $R^4$ and $R^5$, which may be identical or different, denote hydrogen, mercapto, $-NR6R^7$, halogen, nitro, CF3, CN, $-OR^8$, $C_1-C_{10}$-alkyl, $C_2-C_{10}$-alkenyl or $C_2-C_{10}$-alkynyl,
- $R^4$ and $R^5$ denote $C_6-C_{10}$-aryl, aryl-$C_1-C_6$-alkyl, $C_6-C_{10}$-aryloxy;
- $R^6$ denotes hydrogen, $C_3-C_6$-cycloalkyl, $C_1-C_{10}$-alkyl, $C_2-C_{10}$-alkenyl or $C_2-C_{10}$-alkynyl, each of which may be mono- or polysubstituted by phenyl, benzyl or $-OR^8$,
- R6 denotes $C_6-C_{10}$-aryl, preferably phenyl, which may optionally be substituted by halogen, $-OR^8$, $C_1-C_4$-alkyl, preferably $-CH_3$, $-SO_3H$ or $-COOR^8$;
- $R^7$ denotes hydrogen, $C_3-C_6$-cycloalkyl, $C_1-C_{10}$-alkyl, $C_2-C_{10}$-alkenyl or $C_2-C_{10}$-alkynyl, each of which may be mono- or polysubstituted by phenyl, benzyl or $-OR^8$,
- $R^7$ denotes $C_6-C_{10}$-aryl, preferably phenyl, which may optionally be substituted by halogen, $-OR^8$, $C_1-C_4$-alkyl, preferably $-CH_3$, $-SO_3H$ or $-COOR^8$; or
- $R^6$ and $R^7$ together with the nitrogen atom form a saturated or unsaturated 5- or 6-membered ring, which may contain nitrogen, oxygen or sulphur as further heteroatoms, whilst the heterocycle may be substituted by a branched or unbranched alkyl group having 1 to 4 carbon atoms, by phenyl or by benzyl;
- $R^8$ denotes hydrogen, $C_1-C_4$-alkyl, $C_2-C_4$-alkenyl, $C_2-C_4$-alkynyl, a benzyl or phenyl group which is optionally mono- or polysubstituted by OH, chlorine, bromine or $OCH_3$, optionally in the form of their racemates, their enantiomers, in the form of their diastereomers and the mixtures thereof, and optionally the pharmacologically acceptable acid addition salts thereof.

Preferred compounds of general formula (I) are those wherein
- A denotes a 5-membered saturated or unsaturated heterocycle other than 1,2,4-oxadiazole, which may contain 1, 2 or 3 heteroatoms selected from the group comprising oxygen, nitrogen or sulphur and is optionally mono- or polysubstituted by $C_1-C_4$-alkoxy, OH, $=O$ or $C_1-C_4$-alkyl, whilst the $C_1-C_4$-alkyl group may in turn be substituted by fluorine, chlorine, bromine, OH or $-NR^6R^7$;
- X denotes oxygen, sulphur or $NR^6$;
- $R^1$ denotes a $C_1-C_6$-alkyl group which may optionally be mono- or polysubstituted by $=O$, $-CN$, $-CHO$, phenyl, $-COOR^8$, $-CONHSO_2R^8$, $-CONR^6R^7$, $-CH=NOR^8$, $-COR^8$, $-NR^6R^7$, $-NHCOR^8$, $-NHCONR^6R^7$, $-NHCOOR^8$, $-OR8$, $-OCOR^8$, $-OCOOR^8$, $-OCONR^6R^7$, $-SR^8$, $-SOR^8$, $-SO_2R^8$, $-SO_3H$, $-SO_2NR^6R^7$, fluorine, chlorine, bromine or by an N-oxide of the formula $-NOR^6R^7$;
- $R^2$ and $R^3$ which may be identical or different denote hydrogen, SH, $-NR^6R^7$, fluorine, chlorine, bromine, nitro, $CF_3$, CN, $-OR^8$, $C_1-C_6$-alkyl, $C_2-C_6$-alkenyl or $C_2-C_6$-alkynyl,
- $R^2$ and $R^3$ denote phenyl, benzyl, phenyloxy;
- $R^4$ and $R^5$ which may be identical or different denote to hydrogen, SH, $-NR^6R^7$, fluorine, chlorine, bromine, nitro, $CF_3$, CN, $-OR^8$, $C_1-C_6$-alkyl, $C_2-C_6$-alkenyl or $C_2-C_6$-alkynyl,
- $R^4$ and $R^5$ denote phenyl, benzyl, phenyloxy;
- $R^6$ denotes hydrogen, $C_3-C_6$-cycloalkyl, $C_1-C_6$-alkyl, $C_2-C_6$-alkenyl or $C_2-C_6$-alkynyl, each of which may be mono- or polysubstituted by hydroxy, phenyl, benzyl or $C_1-C_4$-alkoxy,
- $R^6$ denotes phenyl, which may optionally be substituted by fluorine, chlorine, bromine, $-OR^8$, $C_1-C_4$-alkyl, preferably $-CH_3$, $-SO_3H$, or $-COOR^8$;
- $R^7$ denotes hydrogen, $C_3-C_6$-cycloalkyl, $C_1-C_6$-alkyl, $C_2-C_6$-alkenyl or $C_2-C_6$-alkynyl, each of which may be mono- or polysubstituted by hydroxy, phenyl, benzyl or $C_1-C_4$-alkoxy,
- $R^7$ denotes phenyl, which may optionally be substituted by fluorine, chlorine, bromine, $-OR^8$, $C_1-C_4$-alkyl, preferably $-CH_3$, $-SO_3H$, or $-COOR^8$; or
- $R^6$ and $R^7$ together with the nitrogen atom form a saturated or unsaturated 5- or 6-membered ring which may contain nitrogen or oxygen as further heteroatoms, whilst the heterocycle may be substituted by $C_1-C_4$-alkyl, phenyl or benzyl;
- $R^8$ denotes hydrogen, $C_1-C_4$-alkyl, $C_2-C_4$-alkenyl, $C_2-C_4$-alkynyl, a benzyl or phenyl group which may optionally be mono- or polysubstituted by OH, chlorine, bromine or $OCH_3$, optionally in the form of their racemates, their enantiomers, in the form of their diastereomers and the mixtures thereof, and optionally the pharmacologically acceptable acid addition salts thereof.

Particularly preferred are compounds of general formula (I) wherein

A denotes a 5-membered saturated or unsaturated heterocycle other than 1,2,4-oxadiazole, which may contain 1, 2 or 3 heteroatoms selected from the group comprising oxygen or nitrogen and is optionally mono- or polysubstituted by $C_1$–$C_4$-alkoxy, OH, =O or $C_1$–$C_4$-alkyl, whilst the $C_1$–$C_4$-alkyl group may in turn be substituted by fluorine, chlorine, bromine, OH or —$NR^6R^7$;

X denotes oxygen;

$R^1$ denotes a $C_1$–$C_4$-alkyl group which is substituted by —$CONHSO_2R^8$, —$CONR^6R^7$, —CH=$NOR^8$, —$NR^6R^7$, —$NHCOR^8$, —$NHCONR^6R^7$, —$NHCOOR^8$, —$OCONR^6R^7$, —$SO_2NR^6R^7$ or by an N-oxide of the formula —$NOR^6R^7$;

$R^2$ and $R^3$ which may be identical or different denote hydrogen, —$NR^6R^7$, fluorine, chlorine, bromine, nitro, $CF_3$, CN, —$OR^8$, $C_1$–$C_4$-alkyl, phenyl, benzyl or phenyloxy;

$R^4$ and $R^5$ which may be identical or different denote hydrogen, —$NR^6R^7$, fluorine, chlorine, bromine, nitro, CF3, CN, —$OR^8$, $C_1$–$C_4$-alkyl, phenyl, benzyl or phenyloxy;

$R^6$ denotes hydrogen, $C_3$–$C_6$-cycloalkyl or $C_1$–$C_4$-alkyl, each of which may be mono- or polysubstituted by hydroxy, phenyl, benzyl or $C_1$–$C_4$-alkoxy, $R^6$ denotes phenyl, which may optionally be substituted by fluorine, chlorine, bromine, —$OR^8$, $C_1$–$C_4$-alkyl, preferably —$CH_3$, —$SO_3H$, or —$COOR^8$;

$R^7$ denotes hydrogen, $C_3$–$C_6$-cycloalkyl or $C_1$–$C_4$-alkyl, each of which may be mono- or polysubstituted by hydroxy, phenyl, benzyl or $C_1$–$C_4$-alkoxy, $R^7$ denotes phenyl, which may optionally be substituted by fluorine, chlorine, bromine, —$OR^8$, $C_1$–$C_4$-alkyl, preferably —$CH_3$, —$SO_3H$, or —$COOR^8$; or $R^6$ and $R^7$ together with the nitrogen atom form a saturated or unsaturated 5- or 6-membered ring which may contain nitrogen or oxygen as further heteroatoms, whilst the heterocycle may be substituted by $C_1$–$C_4$-alkyl, phenyl or benzyl;

$R^8$ denotes hydrogen, $C_1$–$C_4$-alkyl, a benzyl or phenyl group which may optionally be mono- or polysubstituted by OH, chlorine, bromine or $OCH_3$, optionally in the form of their racemates, their enantiomers, in the form of their diastereomers and the mixtures thereof, and optionally the pharmacologically acceptable acid addition salts thereof.

Also preferred according to the invention are compounds of general formula (I) wherein A denotes a furan, tetrahydrofuran, dioxolane, pyrrole, pyrroline, pyrrolidine, pyrazole, pyrazoline, pyrazolidine, imidazole, imidazoline, imidazolidine, triazole, triazoline, triazolidine, oxazole, oxazoline, oxadiazole but not 1,2,4-oxadiazole, isoxazole or isoxazoline, each of which may be mono- or polysubstituted by $C_1$–$C_4$-alkoxy, OH, =O or $C_1$–$C_4$-alkyl, whilst the $C_1$–$C_4$-alkyl group may in turn be substituted by fluorine, chlorine, bromine, OH or —$NR^6R^7$;

X denotes oxygen;

$R^1$ denotes $C_1$–$C_4$-alkyl which is substituted by —$NR^6R^7$ or by an N-oxide of the formula —$NOR^6R^7$;

$R^2$ and $R^3$ which may be identical or different denote hydrogen, —$NR^6R^7$, fluorine, chlorine, bromine, nitro, $CF_3$, CN, —$OR^8$, $C_1$–$C_4$-alkyl, phenyl, benzyl or phenyloxy;

$R^4$ and $R^5$ which may be identical or different denote hydrogen, —$NR^6R^7$, fluorine, chlorine, bromine, nitro, $CF_3$, CN, —$OR^8$, $C_1$–$C_4$-alkyl, phenyl, benzyl or phenyloxy;

$R^6$ denotes hydrogen or $C_1$–$C_4$-alkyl which may be mono- or polysubstituted by hydroxy, phenyl, benzyl or $C_1$–$C_4$-alkoxy, $R^7$ denotes hydrogen or $C_1$–$C_4$-alkyl which may be mono- or polysubstituted by hydroxy, phenyl, benzyl or $C_1$–$C_4$-alkoxy, or $R^6$ and $R^7$ together with the nitrogen atom form a saturated or unsaturated heterocycle selected from the group comprising pyrrole, pyrroline, pyrrolidine, piperidine, piperazine, morpholine, thiomorpholine, imidazole, imidazoline, imidazolidine, pyrazole, pyrazoline, pyrazolidine, whilst the abovementioned heterocycles may optionally be substituted by methyl, ethyl, propyl or benzyl;

$R^8$ denotes hydrogen, $C_1$–$C_4$-alkyl, benzyl or phenyl, optionally in the form of their racemates, their enantiomers, in the form of their diastereomers and the mixtures thereof, and optionally the pharmacologically acceptable acid addition salts thereof.

Of particular interest are compounds of general formula (I), wherein

A denotes a group selected from among pyrrole, pyrazole, imidazole, imidazoline, imidazolidine, triazole, oxazole, oxazoline, isoxazole, 1,3,4-oxadiazole or oxadiazoline which may optionally be mono- or polysubstituted by OH, =O, $C_1$–$C_4$-alkyloxy or by $C_1$–$C_4$-alkyl, whilst the $C_1$–$C_4$-alkyl group may in turn be substituted by chlorine, bromine, OH or —$NR^6R^7$;

X denotes oxygen;

$R^1$ denotes $C_1$–$C_4$-alkyl which is substituted by —$NR^6R^7$;

$R^2$ and $R^3$ denote hydrogen;

$R^4$ and $R^5$ denote hydrogen;

$R^6$ denotes hydrogen, methyl, ethyl, propyl or butyl;

$R^7$ denotes hydrogen, methyl, ethyl, propyl or butyl; or $R^6$ and $R^7$ together with the nitrogen atom form a saturated or unsaturated heterocycle selected from the group comprising piperidine, piperazine or morpholine which may optionally be substituted by methyl, ethyl or benzyl, optionally in the form of their racemates, their enantiomers, in the form of their diastereomers and the mixtures thereof, and optionally the pharmacologically acceptable acid addition salts thereof.

Of particular interest are compounds of general formula (I) wherein

A denotes a group selected from among pyrrole, pyrazole, imidazole, imidazoline, imidazolidine, triazole, oxazole, oxazoline, isoxazole, 1,3,4-oxadiazole or oxadiazoline which may optionally be mono- or polysubstituted by OH, =O, $C_1$–$C_4$-alkyloxy or by $C_1$–$C_4$-alkyl, whilst the $C_1$–$C_4$-alkyl group may in turn be substituted by chlorine, bromine, OH or —$NR^6R^7$;

X denotes oxygen;

$R^1$ denotes an ethyl or propyl group which is substituted by —$NR^6R^7$;

$R^2$ and $R^3$ denote hydrogen;

$R^4$ and $R^5$ denote hydrogen;

$R^6$ denotes hydrogen, methyl, ethyl, propyl or butyl;

$R^7$ hydrogen, methyl, ethyl, propyl or butyl, optionally in the form of their racemates, their enantiomers, in the form of their diastereomers and the mixtures thereof, and optionally the pharmacologically acceptable acid addition salts thereof.

Particularly preferred according to the invention are compounds of general formula (I) wherein the group

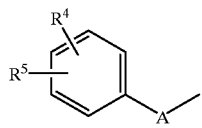

may denote one of the following groups

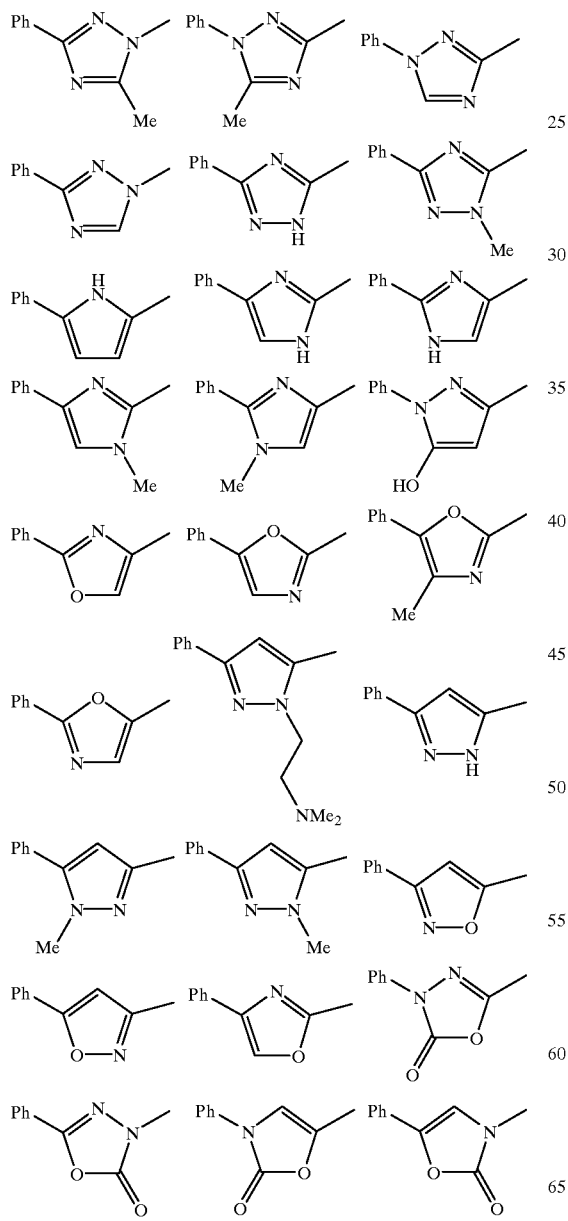

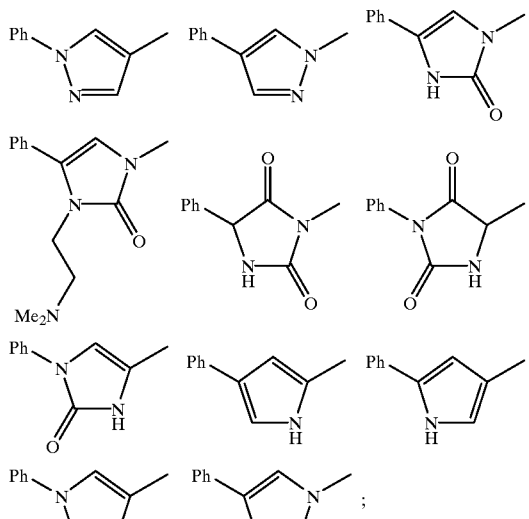

X denotes oxygen;

$R^1$ denotes an ethyl or propyl group which is substituted by $-NR^6R^7$;

$R^2$ and $R^3$ denote hydrogen;

$R^4$ and $R^5$ denote hydrogen;

$R^6$ denotes hydrogen, methyl, ethyl, propyl or butyl;

$R^7$ denotes hydrogen, methyl, ethyl, propyl or butyl,
optionally in the form of their racemates, their enantiomers, in the form of their diastereomers and the mixtures thereof, optionally in the form of their tautomers, and optionally the pharmacologically acceptable acid addition salts thereof.

Compounds of general formula (I) which are also particularly preferred according to the invention are those wherein the group

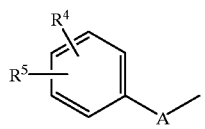

may represent one of the following groups:

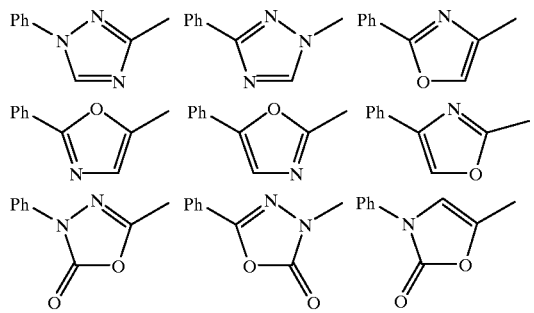

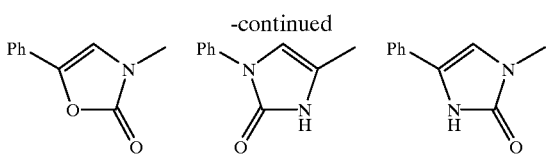

X denotes oxygen;

R¹ denotes an ethyl or propyl group which is substituted by —NR⁶R⁷;

R² and R³ denote hydrogen;

R⁴ and R⁵ denote hydrogen;

R⁶ denotes hydrogen, methyl, ethyl, propyl or butyl;

R⁷ denotes hydrogen, methyl, ethyl, propyl or butyl, optionally in the form of their racemates, their enantiomers, in the form of their diastereomers and the mixtures thereof, optionally in the form of their tautomers, and optionally the pharmacologically acceptable acid addition salts thereof.

Also of particular importance are compounds of general formula (I), wherein the group

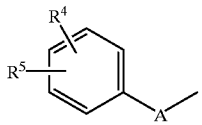

may represent one of the following groups:

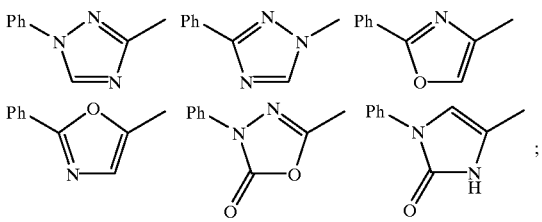

X denotes oxygen;

R¹ denotes —CH₂–CH₂—NR⁶R⁷;

R² and R³ denote hydrogen;

R⁴ and R⁵ denote hydrogen;

R⁶ denotes methyl;

R⁷ denotes methyl, optionally in the form of their racemates, their enantiomers, in the form of their diastereomers and the mixtures thereof, optionally in the form of their tautomers, and optionally the pharmacologically acceptable acid addition salts thereof.

The following compounds are mentioned as being particularly preferred:

-3-{2-[2(N,N-Dimethylamino)ethyl]oxy-phenyl}-1-phenyl-1,2,4-triazole; -1-{2-[2(N,N-Dimethylamino)ethyl]oxy-phenyl}-3-phenyl-1,2,4-triazole; -4-{2-[2(N,N-Dimethylamino)ethyl]oxy-phenyl}-2-phenyl-1,3-oxazole; -5-{2-[2(N,N-Dimethylamino)ethyl]oxy-phenyl}-2-phenyl-1,3-oxazole.

Examples of alkyl groups (including those which are part of other groups such as alkylene bridges) include, unless otherwise specified, branched and unbranched alkyl groups with 1 to 10 carbon atoms, preferably 1–4 carbon atoms, such as: methyl, ethyl, n-propyl, iso-propyl, butyl, iso-butyl, sec. butyl, tert.-butyl, pentyl, iso-pentyl, hexyl, heptyl and octyl. The groups methyl, ethyl, butyl or tert.-butyl are also referred to by the abbreviations Me, Et, Bu or tBu.

Substituted alkyl groups (including those which are part of other groups) may, unless otherwise specified, carry one or more of the following substituents: halogen, hydroxy, mercapto, $C_1$–$C_6$-alkyloxy, amino, alkylamino, dialkylamino, cyano, nitro, =O, —CHO, —COOH, —COO—$C_1$–$C_6$-alkyl, —S—$C_1$–$C_6$-alkyl.

Examples of alkenyl groups (including those which are part of other groups) include branched and unbranched alkenyl groups with 2 to 10 carbon atoms, preferably 2 to 3 carbon atoms, if they have at least one double bond, for example the abovementioned alkyl groups as well if they have at least one double bond, such as vinyl (provided that no unstable enamines or enolethers are formed), propenyl, iso-propenyl, butenyl, pentenyl, hexenyl.

Substituted alkenyl groups, unless otherwise specified (including those which are part of other groups), may for example carry one or more of the following substituents: halogen, hydroxy, mercapto, $C_1$–$C_6$-alkyloxy, amino, alkylamino, dialkylamino, cyano, nitro, =O, —CHO, —COOH, —COO—$C_1$–$C_6$-alkyl, —S—$C_1$–$C_6$-alkyl.

Examples of alkynyl groups (including those which are part of other groups) include alkynyl groups with 2 to 10 carbon atoms, provided that they have at least one triple bond, for example ethinyl, propargyl, butinyl, pentinyl, hexinyl.

Substituted alkynyl groups, unless otherwise specified (including those which are part of other groups), may for example carry one or more of the following substituents: halogen, hydroxy, mercapto, $C_1$–$C_6$-alkyloxy, amino, alkylamino, dialkylamino, cyano, nitro, =O, —CHO, —COOH, —COO—$C_1$–$C_6$-alkyl, —S—$C_1$–$C_6$-alkyl.

Examples of cycloalkyl groups with 3–6 carbon atoms include cyclopropyl, cyclobutyl, cyclopentyl or cyclohexyl, which may also be substituted by branched or unbranched alkyl having 1 to 4 carbon atoms, hydroxy and/or halogen or may be substituted as specified hereinbefore. The term halogen generally refers to fluorine, chlorine, bromine or iodine.

The term aryl represents an aromatic ring system with 6 to 10 carbon atoms which, unless otherwise specified, may for example carry one or more of the following substituents: $C_1$–$C_6$-alkyl, $C_1$–$C_6$-alkyloxy, halogen, hydroxy, mercapto, amino, alkylamino, dialkylamino, $CF_3$, cyano, nitro, —CHO, —COOH, —COO—$C_1$–$C_6$-alkyl, —S—$C_1$–$C_6$-alkyl. The preferred aryl group is phenyl.

Examples of N-linked cyclic groups of general formula NR⁶R⁷ include: pyrrole, pyrroline, pyrrolidine, 2-methylpyrrolidine, 3-methylpyrrolidine, piperidine, piperazine, N-methylpiperazine, N-ethylpiperazine, N-(n-propyl)-piperazine, N-benzylpiperazine, morpholine, thiomorpholine, imidazole, imidazoline, imidazolidine, pyrazole, pyrazoline, pyrazolidine, preferably morpholine, N-benzylpiperazine, piperazine and piperidine, whilst the abovementioned heterocycles may be substituted by alkyl having 1 to 4 carbon atoms, preferably methyl.

"=O" denotes an oxygen atom linked via a double bond.

The present invention relates to compounds which surprisingly have a high affinity for the following receptor type: "Na⁺ channel site 2" binding site. In addition, these compounds exhibit an antagonistic activity at the AMPA receptor. In the light of these findings the compounds according to the invention may be used in neurodegenerative disorders and cerebral ischaemia of various origins.

The compounds according to the invention may be prepared by using known analogous methods. Thus, for example, compounds of general formula (II)

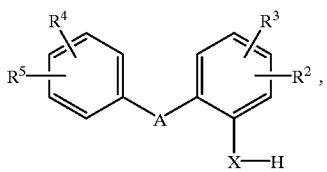

(II)

wherein A, X and the groups $R^2$, $R^3$, $R^4$ and $R^5$ are as hereinbefore defined, are reacted under basic conditions with electrophiles of general formula

L-R¹, wherein L denotes a leaving group such as for example chlorine, bromine, iodine, methanesulphonyl, trifluoromethanesulphonyl or p-toluenesulphonyl and $R^1$ is as hereinbefore defined, with alkylation to the compounds of general formula (I).

The following synthesis instructions serve to illustrate the analogous methods which may be used to prepare the compounds according to the invention, without restricting the invention to their subject matter.

EXAMPLE 1

1,3-Diphenyl-1,2,4-triazole

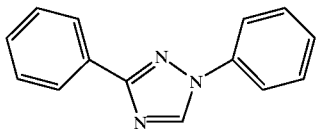

a) benzoylimidoethylester-hydrochloride:

At about 0° C. HCl gas is piped into a solution of 100 g of benzonitrile and 60 ml of ethanol over a period of about 3 hours (weight increase: about 65 g). The mixture obtained is then left to stand for 6 days at −25° C. After heating to 0° C. it is stirred with ether and the crystalline residue thus obtained is suction filtered, washed with ether and dried. The imidoether hydrochloride thus obtained (139.5 g–78% of theory) is used in the next step of the reaction without further purification.

b) imidohydrazide:

3.7 g of benzoylimidoethylester-hydrochloride and 2.2 g of phenylhydrazine are refluxed in 50 ml of anhydrous ethanol over a period of 1.5 hours.

Then the solvent is distilled off in vacuo and the residue remaining is taken up in water. After extraction with diethylether the aqueous phase is made alkaline with aqueous ammonia solution and extracted again with diethylether. The combined organic phases are dried over $Na_2SO_4$. After distilling off the solvent in vacuo, 2.3 g (54%) of the imidohydrazide remain in the form of slightly red crystals. There is no further purification.

c) 1,3-Diphenyl-1,2,4-triazole 2 g of imidohydrazide are taken up in 5 ml of formic acid (98%) and refluxed for 2 hours. After cooling to ambient temperature the mixture is carefully adjusted to pH=8 with 10% $Na_2CO_3$ solution and the mixture obtained is extracted twice with ethyl acetate. The combined organic phases are dried over $MgSO_4$ and the solvent distilled off in vacuo. The residue remaining is purified by chromatography on silica gel (dichloromethane:methanol 95:5) and then converted into the hydrochloride. Yield: 0.7 g (30%), melting point: 80° C.;

EXAMPLE 2

1-(2-methoxyphenyl)-3-phenyl-1,2,4-triazole

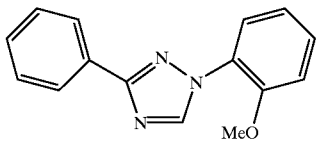

a) imidohydrazide formation:

4.6 g of benzoylimidoethylester-hydrochloride (cf. Example 1, step a) and 3.5 g of 2-methoxy-phenylhydrazine are refluxed in 80 ml of anhydrous ethanol over a period of 4–5 hours. Then the solvent is distilled off in vacuo and the residue remaining is taken up in dilute aqueous HCl solution. After extraction with diethylether the aqueous phase is made alkaline with aqueous ammonia solution and extracted again with diethylether. The combined organic phases are dried over $Na_2SO_4$. After the solvent has been distilled off in vacuo 2,5 g (41%) of the imidohydrazide are left in the form of a brown oil. No further purification is carried out.

b) 1-(2-methoxyphenyl)-3-phenyl-1,2,4-triazole 2,4 g of imidohydrazide are taken up in 10 ml of formic acid (98%-ig) and refluxed for 8–9 hours. After cooling to ambient temperature the mixture is poured onto ice and the resulting mixture is extracted twice with ethyl acetate. The combined organic phases are dried over $MgSO_4$ and the solvent distilled off in vacuo. The residue remaining is purified by chromatography on silica gel (toluene: ethyl acetate 90:10).

Yield: 1,2 g (48%), melting point: 83–84° C.;

EXAMPLE 3

1-{2-[2(N,N-Dimethylamino)ethyl]oxy-phenyl}-3-phenyl-1,2,4-triazole

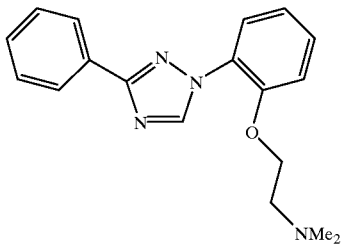

a) 1-(2-hydroxyphenyl)-3-phenyl-1,2,4-triazole 1,1 g of 1-(2-methoxyphenyl)-3-phenyl-1,2,4-triazole (cf. Example 2) are dissolved in 40 ml of dichloromethane and a solution of 1 ml of $BBr_3$ in 10 ml of dichloromethane is added dropwise. After 3–4 hours stirring at ambient temperature the mixture is poured onto ice water and the organic phase is separated off. The remaining aqueous phase is again extracted with dichloromethane. After the collected dichloromethane phases have been dried over $Na_2SO_4$ the solvent is distilled off. 1 g (96%) of the title compound are left (melting point: 148–154° C.).

b) 1-{2-[2(N,N-Dimethylamino)ethyl]oxy-phenyl}-3-phenyl-1,2,4-triazole 0,94 g of 1-(2-hydroxyphenyl)-3-phenyl-1,2,4-triazole are dissolved in 25 ml of DMF and 0.18 g of sodium hydride (60% in oil) are added. The mixture is then stirred for a further 30 minutes at ambient temperature and a mixture of 1,15 g of 2-N,N-dimethylaminoethylchloride and 0.36 g of sodium hydride (60% in oil) in 25 ml of DMF which has previously been stirred for 5 minutes is added. This mixture is heated to 100° C. for 4 hours, and then the solvent is eliminated in vacuo. The residue is taken up in 2 N hydrochloric acid and extracted with ethyl acetate. The aqueous phase is made alkaline with aqueous ammonia solution and extracted twice with dichloromethane. The organic phase is dried over sodium sulphate, evaporated down in vacuo and chromatographed on silica gel (methanol).

Yield: 500 mg (41%), light-coloured oil; melting point (fumarate): 184–186° C.;

EXAMPLE 4

1-{2-[2(N,N-Dimethylamino)ethyl]oxy-phenyl}-5-methyl-3-phenyl-1,2,4-triazole

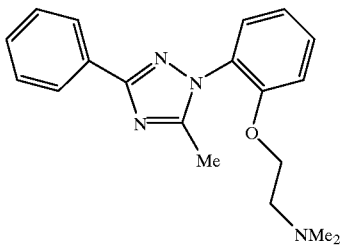

a) imidohydrazide formation:

2.5 g of the benzoylimidoethylester-hydrochloride obtained according to Example 1 (step a) and 2.9 g of 2-benzyloxy-phenylhydrazine are refluxed in 40 ml of anhydrous ethanol over a period of 2 hours. Then the solvent is distilled off in vacuo and the residue remaining is taken up in dilute aqueous HCl solution. After extraction with diethylether the aqueous phase is made alkaline with aqueous ammonia solution and extracted again with diethylether. The combined organic phases are dried over sodium sulphate. After the solvent has been distilled off in vacuo 1.6 g (37%) of the imidohydrazide remain in the form of light brown crystals. No further purification is carried out.

b) 1-(2-benzyloxyphenyl)-5-methyl-3-phenyl-1,2,4-triazole 1,55 g of imidohydrazide are taken up in 4,1 g of triethyl orthoacetate in 30 ml of anhydrous ethanol and refluxed for 6 hours. After cooling to ambient temperature the solvent is distilled off in vacuo and the residue remaining is taken up in diethylether. The organic phase thus obtained is washed three times with water, dried over MgSO$_4$ and the solvent is distilled off in vacuo. The crude product remaining is purified by chromatography on silica gel (toluene: ethyl acetate 80:20).

Yield: 1,1 g (64%), slightly brownish oil;

c) 1-(2-hydroxyphenyl)-5-methyl-3-phenyl-1,2,4-triazole 1 g of 1-(2-benzyloxyphenyl)-5-methyl-3-phenyl-1,2,4-triazole are dissolved in 20 ml of anhydrous dichloromethane and a solution of 0,5 ml of BBr$_3$ in 10 ml of dichloromethane is added dropwise. After 3 hours stirring at ambient temperature the mixture is diluted with a further 100 ml of dichloromethane and washed twice with water. After the organic phase has been dried over Na$_2$SO$_4$ the solvent is distilled off. The crude product remaining is purified by chromatography on silica gel (toluene:ethyl acetate 80:20).

Yield: 0.6 g (82%); melting point: 198–199° C., colourless crystals;

d) 1-{2-[2(N,N-Dimethylamino)ethyl]oxy-phenyl}-5-methyl-3-phenyl-1,2,4-triazole 0,69 g of 2-N,N-dimethylaminoethylchloride×HCl are added to 10 ml of 1,4-dioxane and 2 ml of water, combined with 0,69 g of potassium carbonate and stirred for 30 minutes at ambient temperature. Then a solution of 0.6 g of 1-(2-hydroxyphenyl)-5-methyl-3-phenyl-1,2,4-triazole in 5 ml of 1,4-dioxane and a suspension of 0.27 g of potassium-tert.butoxide in 5 ml of 1,4-dioxane are added slowly. The resulting mixture is stirred for 3 hours at about 100° C. Then the solvent is distilled off in vacuo, the residue remaining is taken up in ethyl acetate and the resulting organic phase is extracted first with water, then with 2N-HCl solution (aq.). The aqueous phases are made alkaline with aqueous ammonia solution and extracted with ethyl acetate. After the combined organic phases have been dried over MgSO$_4$ the solvent is distilled off in vacuo. The crude product remaining is purified by chromatography on silica gel (dichloromethane:methanol 80:20). The resulting title compound is converted into the dihydrochloride.

Yield: 0,4 g (42%); melting point: 170° C. (decomposition), colourless crystals.

EXAMPLE 5

3-{2-[2(N,N-Dimethylamino)ethyl]oxy-phenyl}-1-phenyl-1,2,4-triazole

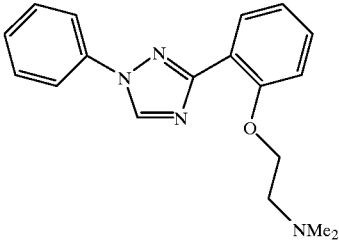

a) 2-hydroxy-benzoylimidoethylester-hydrochloride:

At about 0° C. HCl gas is piped into a solution of 60 g of 2-cyanophenol and 60 ml of ethanol in 500 ml of anhydrous diethylether over a period of about 3 hours. The mixture obtained is stirred for 2 hours at constant temperature and then left to stand for several days. The crystalline precipitate is suction filtered, washed with ether and dried. The resulting imidoether hydrochloride (49.1 g of=48%; melting point: 130–131° C.) is used in the next reaction step without further purification.

b) imidohydrazide formation:

4 g of the 2-hydroxy-benzoylimidoethylester-hydrochloride prepared beforehand and 2.2 g of phenylhydrazine are refluxed in 50 ml of anhydrous ethanol over a period of 2 hours. Then the solvent is distilled off in vacuo and the residue remaining is taken up in dilute aqueous HCl solution. After extraction with diethylether the aqueous phase is made alkaline with aqueous ammonia solution and extracted again with diethylether. The combined organic phases are dried over sodium sulphate. After the solvent has been distilled off in vacuo 3,4 g (75%) of the imidohydrazide are left in the form of slightly red crystals (melting point: 154° C. and decomposition). No further purification is carried out.

c) 3-(2-hydroxyphenyl)-1-phenyl-1,2,4-triazole 3 g of imidohydrazide are taken up in 7,5 ml of formic acid (98%) and refluxed for 10 hours. After cooling to ambient temperature the mixture is poured onto ice and carefully neutralised with 10% Na$_2$CO$_3$ solution (aq.). The mixture obtained is extracted twice with ethyl acetate. The combined organic phases are dried over sodium sulphate and the solvent is distilled off in vacuo. The residue remaining is purified by chromatography on silica gel (toluene:ethyl acetate 80:20).

Yield: 2.6 g (84%), melting point: 105° C.

d) 3-{2-[2(N,N-Dimethylamino)ethyl]oxy-phenyl}-1-phenyl-1,2,4-triazole 2.37 g of 3-(2-hydroxyphenyl)-1-phenyl-1,2,4-triazole are dissolved in 50 ml of DMF and combined with 0.44 g of sodium hydride (60% in oil). The mixture is then stirred for a further 30 minutes at ambient temperature and a mixture of 2.88 g of 2-N,N-dimethylaminoethylchloride and 0.88 g of sodium hydride (60% in oil) previously stirred for 5 minutes is then added to 50 ml of DMF. This mixture is heated to 100° C. for 4 hours, and then the solvent is eliminated in vacuo. The residue is taken up in 2 N HCl solution (aq.) and extracted with ethyl acetate. The aqueous phase is made alkaline with aqueous ammonia solution and extracted with dichloromethane. The organic phase is dried over sodium sulphate, evaporated down in vacuo and chromatographed on silica gel (methanol). After purification the title compound is converted into the hydrochloride.

Yield: 2.5 g (72%), melting point (hydrochloride): 187–198° C.;

EXAMPLE 6

3-{2-[2(N,N-Dimethylamino)ethyl]oxy-phenyl}-5-methyl-1-phenyl-1,2,4-triazole

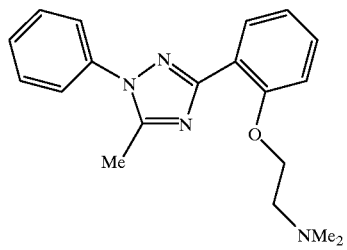

a) 3-(2-hydroxyphenyl)-5-methyl-1-phenyl-1,2,4-triazole 3,4 g of the imidohydrazide prepared according to Example 5 (step b) are taken up with 12.1 g of triethyl orthoacetate in 50 ml of anhydrous ethanol and refluxed for 6 hours. After cooling to ambient temperature the solvent is distilled off in vacuo and the residue remaining is taken up in diethylether. The resulting organic phase is washed three times with water, dried over MgSO$_4$ and the solvent is distilled off in vacuo. The crude product remaining is purified by chromatography on silica gel (toluene:ethyl acetate 80:20).

Yield: 2 g (53%), slightly brownish oil;

b) 3-{2-[2(N,N-Dimethylamino)ethyl]oxy-phenyl}-5-methyl-1-phenyl-1,2,4-triazole 2,3 g of 2-N,N-dimethylaminoethylchloride×HCl are added to 10 ml of 1,4-dioxane and 2 ml of water, combined with 2.8 g of potassium carbonate and stirred for 30 minutes at ambient temperature. Then a solution of 2,0 g of 3-(2-hydroxyphenyl)-5-methyl-1-phenyl-1,2,4-triazole in 10 ml of 1,4-dioxane and a suspension of 0.9 g of potassium-tert.butoxide in 5 ml of 1,4-dioxane are added slowly. The resulting mixture is stirred for 3 hours at about 100° C. Then the solvent is distilled off in vacuo, the residue remaining is taken up in ethyl acetate and the resulting organic phase is extracted with water, then with 2N-HCl solution (aq.). The aqueous phases are made alkaline with aqueous ammonia solution and extracted with ethyl acetate. After the combined organic phases have been dried over MgSO$_4$ the solvent is distilled off in vacuo. The crude product remaining is purified by chromatography on silica gel (dichloromethane:methanol 80:20). The resulting title compound is converted into the dihydrochloride.

Yield: 1.2 g (38%); melting point: 85° C. (decomposition), colourless crystals;

EXAMPLE 7

3-{2-[2(N,N-Dimethylamino)ethyl]oxy-phenyl}-5-phenyl-1,2,4-triazole

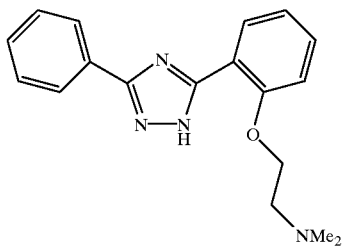

a) 2-phenyl-benzofe[1,3]oxazin-4-one:

This is prepared by a method known from the literature (J. Chem. Soc. 1910, 208).

b) 3-(2-hydroxyoxyphenyl)-5-phenyl-1,2,4-triazole:

1.9 g of 2-phenyl-benzo[e][1,3]oxazin-4-one are refluxed in 75 ml of ethanol with 1.0 g of hydrazine hydrate. After about 1 hour the solvent is distilled off in vacuo and the residue remaining is stirred into water. The solid formed (3-(2-hydroxyphenyl)-5-phenyl-1,2,4-triazole) is used in the next step without further purification. Yield: 0.5 g (25%).

c) 3-{2-[2(N,N-Dimethylamino)ethyl]oxy-phenyl}-5-phenyl-1,2,4-triazole 0,85 g of 3-(2-hydroxyphenyl)-5-phenyl-1,2,4-triazole are stirred with 4 mmol of sodium methoxide at ambient temperature for 15 minutes in anhydrous methanol (20 ml). After the solvent has been distilled off in vacuo 20 ml of DMF are added and the resulting solution is added to a mixture of 0.87 g of 2-N,N-dimethylaminoethylchloride and 0.24 g of sodium hydride (60% in oil) in 20 ml of DMF which has previously been stirred for 30 minutes. This mixture is heated for 2 hours to 100° C., and then the solvent is eliminated in vacuo. The residue is taken up in water and extracted twice with dichloromethane. The organic phase is dried over sodium sulphate, evaporated down in vacuo and chromatographed on silica gel (ethyl acetate:isopropanol 70:30). After the purification the title compound is converted into the hydrochloride.

Yield: 0.14 g (11%), melting point (hydrochloride): 207–208° C.;

EXAMPLE 8

4-{2-[2(N,N-dimethylamino)ethyl]oxy-phenyl}-2-phenyl-1,3-oxazole

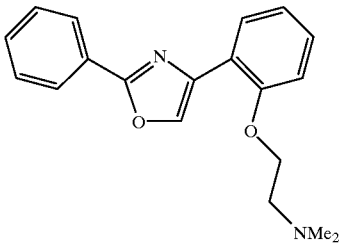

a) 2-benzyloxyacetophenone:

2,3 g of sodium are dissolved in 150 ml of anhydrous methanol and combined with 13.6 g of 2-hydroxyacetophenone. After 10 minutes stirring at ambient temperature 17.1 g of benzylbromide and 10 ml of DMF are added. The mixture is refluxed for about 4 hours. To work it up the solvent is distilled off in vacuo, the residue is taken up in ethyl acetate and washed with water. The aqueous phase is again extracted with ethyl acetate. After the combined organic phases have been dried over $Na_2SO_4$ the solvent is distilled off in vacuo. 19 g (84%) 2-benzyloxyacetophenone remain, which can be used in the next step without further purification.

b) 1-(2-benzyloxy-phenyl)-2-hydroxy-ethanone:

2,26 g of the 2-benzyloxyacetophenone from step (a) are taken up in 3,54 g of diacetoxyphenyl-8³-iodane in 22 ml of methanol and at about 10° C. a solution of 1.2 g of NaOH in 22 ml of methanol is added slowly with stirring. After one hour's stirring at ambient temperature the mixture is acidified with 2N HCl solution (aq.) whilst cooling and extracted twice with dichloromethane. After the combined organic phases have been dried over $Na_2SO_4$ the solvent is distilled off in vacuo and the residue remaining is chromatographed on silica gel (toluene:ethyl acetate 80:20). Yield: 1,3 g (54%);

c) 2-benzyloxy-1-(2-benzyloxy-phenyl)-ethanone:

A solution of 0.73 g of benzoic acid in 20 ml of anhydrous tetrahydrofuran is combined with 1,23 g of N,N-dicyclohexylcarbodiimide and then a solution of 1,3 g of 1-(2-benzyloxy-phenyl)-2-hydroxy-ethanone is added dropwise according to step (b). After the final addition of 100 mg of N,N-dimethylaminopyridine the mixture is stirred for about 12 hours at ambient temperature and the precipitate obtained is separated off. The solvent is distilled off in vacuo and the residue remaining is chromatographed on silica gel (toluene:ethyl acetate 80:20). Yield: 0.95 g (51%);

d) 4-(2-benzyloxyphenyl)-2-phenyl-1,3-oxazole 3.46 g of 2-benzyloxy-1-(2-benzyloxy-phenyl)-ethanone according to step (c) are refluxed with 2.95 g of acetamide and 0.9 ml of boron trifluoride etherate in 100 ml of anhydrous xylene over 20 hours. After the solution obtained has been cooled and washed with water it is dried over sodium sulphate, the solvent is distilled off in vacuo and the residue remaining is chromatographed on silica gel (toluene). In addition to re-isolated educt, 1 g (31%) of the target compound is isolated.

e) 4-(2-hydroxyphenyl)-2-phenyl-1,3-oxazole 0.7 g of 4-(2-benzyloxyphenyl)-2-phenyl-1,3-oxazole according to step (d) are hydrogenated in 30 ml of tetrahydrofuran in the presence of 0.1 g of Pd/C catalyst at 20–60° C. (5 bar). After the catalyst has been separated off the solvent is distilled off in vacuo and the residue remaining is chromatographed on silica gel (dioxane:hexane 1:5). Yield: 0.5 g (99%);

f) 4-{2-[2(N,N-dimethylamino)ethyl]oxy-phenyl}-2-phenyl-1,3-oxazole 0.48 g of 4-(2-hydroxyphenyl)-2-phenyl-1,3-oxazole are dissolved in 6 ml of DMF and at 0° C. slowly combined with 2 ml of a 1 molar solution of lithiumhexamethyldisilazide in hexane. After 15 minutes stirring at ambient temperature, a mixture of 0.86 g of 2-N,N-dimethylaminoethylchlorid-hydrochloride and 6 mmol of lithiumhexamethyldisilazane in 8 ml of DMF previously stirred for 30 minutes is added dropwise. This mixture is refluxed for 8 hours and then the solvent is eliminated in vacuo. The residue is taken up in water and extracted twice with ethyl acetate. The organic phase is dried over sodium sulphate, evaporated down in vacuo and chromatographed on silica gel (ethyl acetate:isopropanol 70:30). After the purification the title compound is converted into the hydrochloride.

Yield: 0.2 g (29%), melting point (hydrochloride): 245–246° C.;

EXAMPLE 9

4-{2-[2(N,N-dimethylamino)ethyl]oxy-phenyl}-2-phenyl-imidazole

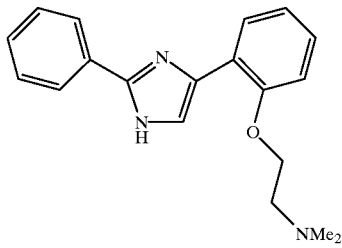

a) 1-(2-benzyloxy-phenyl)-2-brom-ethanone:

2.9 g of 2-benzyloxyacetophenone (Example 8, step (a)) are taken up in 50 ml of anhydrous chloroform and at about 2° C. slowly combined with a solution of 2.1 g of bromine in 10 ml of anhydrous chloroform, with stirring. After conversion is complete the solvent is distilled off in vacuo and the residue remaining is chromatographed on silica gel (toluene).

Yield: 2,3 g (59%);

b) 4-(2-benzyloxyphenyl)-2-phenyl-1,3-imidazole 1.5 g of 1-(2-benzyloxy-phenyl)-2-bromo-ethanone according to step (a) are refluxed with 2,4 g of benzamidine-hydrochloride in 30 ml of anhydrous chloroform over 3 hours. After cooling and distilling off the solvent in vacuo the residue is taken up in dichloromethane and washed with water. The organic phase separated off is dried over sodium sulphate, the solvent is distilled off in vacuo and the residue remaining is chromatographed on silica gel (dichloromethane:methanol 98:2).

Yield: 1.2 g (82%);

c) 4-(2-benzyloxyphenyl)-1-tert.butoxycarbonyl-2-phenyl-1,3-imidazole 1,7 g of 4-(2-benzyloxyphenyl)-2-phenyl-1,3-imidazole according to step (b) are added, with 0.3 g of N,N-dimethylaminopyridine, to 50 ml of anhydrous tetrahydrofuran and at about 10° C. a solution of 2,18 g of di-tert.-butyldicarbonate ($BOC_2O$) in 20 ml of anhydrous tetrahydrofuran is added dropwise with stirring. After 3 hours' stirring at ambient temperature and distilling off the solvent in vacuo the residue is taken up in ethyl acetate and washed successively with $KHSO_4$ solution, $NaHCO_3$ solution and NaCl solution. The organic phase separated off is dried over sodium sulphate and the solvent is distilled off in vacuo. Yield: 2.2 g (99%);

d) 1-tert.Butoxycarbonyl-4-(2-hydroxyphenyl)-2-phenyl-1,3-imidazole 2.2 g of 4-(2-benzyloxyphenyl)-1-tert.butoxycarbonyl-2-phenyl-1,3-imidazole according to step (c) are hydrogenated in 35 ml of tetrahydrofuran in the presence of 0.2 g of Pd/C catalyst at ambient temperature (5 bar). After the catalyst has been separated off the solvent is distilled off in vacuo and the residue remaining is chromatographed on silica gel (toluene).
Yield: 0.75 g (43%);

e) 1-tert.Butoxycarbonyl-4-{2-[2(N,N-dimethylamino)ethyl]oxy-phenyl}-2-phenyl-imidazole 1,15 g of 1-tert.butoxycarbonyl-4-(2-hydroxyphenyl)-2-phenyl-1,3-imidazole are dissolved in 15 ml of DMF and combined with 0.136 g of sodium hydride (60% in oil). The mixture is then stirred for 30 minutes at ambient temperature and a mixture of 0.72 g of 2-N,N-dimethylaminoethylchloride-hydrochloride and 0.2 g of sodium hydride (60% in oil) in 20 ml of DMF previously stirred for 30 minutes is then added. This mixture is heated to 100° C. for 2 hours, and then the solvent is eliminated in vacuo. The residue is taken up in water and extracted twice with dichloromethane. The combined organic phases are dried over sodium sulphate, evaporated down in vacua and chromatographed on silica gel (dioxane:hexane 1:5).
Yield: 0.75 g (54%);

f) 4-{2-[2(N,N-dimethylamino)ethyl]oxy-phenyl}-2-phenyl-imidazole 0.75 g of 1-tert.butoxycarbonyl-4-{2-[2(N,N-dimethylamino)ethyl]oxy-phenyl}-2-phenyl-imidazole in 5 ml of ethanol are combined with 20 ml of a 2 M solution of HCl in ethyl acetate, stirred for 4 hours at ambient temperature and then the solvent is eliminated in vacua. The residue is taken up in water, made alkaline with aqueous ammonia solution and extracted twice with diethylether. The organic phase is dried over sodium sulphate, evaporated down in vacuo and chromatographed on silica gel (ethyl acetate:isopropanol 70:30). After the purification the title compound is converted into the dihydrochloride.
Yield: 0.27 g (396), melting point (hydrochloride): 155–158° C.;

EXAMPLE 10

5-{2-[2(N,N-dimethylamino)ethyl]oxy-phenyl}-2-phenyl-1,3-oxazole

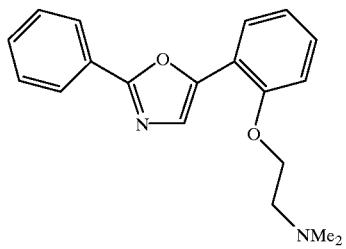

a) 2-amino-1-(2-benzyloxy-phenyl)-ethanone:

2 g of 1-(2-benzyloxy-phenyl)-2-bromo-ethanone (Example 9, step (a)) are taken up in 15 ml of anhydrous chloroform and combined with a solution of 1,8 g of urotropin in 40 ml of anhydrous chloroform. After 6 hours stirring at ambient temperature the precipitate obtained is separated off and the remaining solution is evaporated down. After the solvent has been distilled off in vacuo the residue remaining is dissolved in ethanol, combined with 5 ml of conc. hydrochloric acid whilst cooling and left to stand for 12 hours at ambient temperature. The solvent is distilled off in vacuo and the crude product obtained is used in the next step without further purification. Yield: 2,4 g (crude product).

b) 2-benzoylamino-1-(2-benzyloxy-phenyl)-ethanone: 1,66 g of the crude product from step (a) are taken up in 50 ml of anhydrous tetrahydrofuran and 10 ml of pyridine, 5 ml of dimethylformamide, 5 ml of triethylamine and 2 ml of benzoic acid chloride are added successively and the resulting mixture is stirred at elevated temperature (about 45° C.). After the conversion is complete the solvent is distilled off, the residue is taken up in dichloromethane and the organic phase is washed with water. After the organic phase has been dried over Na$_2$SO$_4$ the solvent is distilled off in vacuo and the residue remaining is chromatographed on silica gel (toluene:ethyl acetate 90:10). Yield: 0.6 g (30%);

c) 5-(2-benzyloxyhenyl)-2-phenyl-1,3-oxazole 0.6 g of 2-benzoylamino-1-(2-benzyloxy-phenyl)-ethanone according to step (b) are heated to 110–115° C. with 10 ml of phosphorus oxychloride for 2 hours with stirring. After cooling the mixture is poured onto ice, made alkaline with aqueous ammonia solution and extracted twice with ethyl acetate. The combined organic phases are dried over sodium sulphate, the solvent is distilled off in vacuo and the residue remaining is chromatographed on silica gel (dioxane:hexane 1:5).
Yield: 0.55 g (96:).

EXAMPLE 11

5-(2-methoxyphenyl)-3-phenyl-1,3,4-oxadiazol-2-one

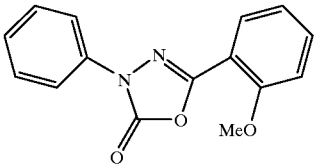

3,2 ml of trichloromethylchloroformate (diphosgene) are added, with stirring, to a solution of 6,3 g of ethyl N'-methoxybenzoyl-N-phenyl-hydrazine-carboxylate in anhydrous tetrahydrofuran at ambient temperature. After one hour's stirring at ambient temperature the solvent is distilled off in vacuo and the residue remaining is recrystallised from ethanol. Yield: 6.5 g (96%), melting point: 112–115° C.

EXAMPLE 12

5-{2-[2(N,N-dimethylamino)ethyl]oxy-phenyl}-3-phenyl-1,3,4-oxadiazol-2-one

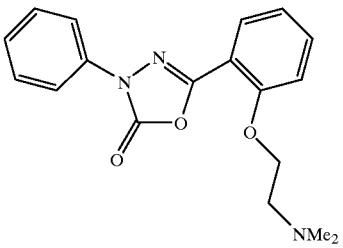

a) 5-(2-hydroxyphenyl)-3-phenyl-1,3,4-oxadiazol-2-one:

6,4 g of 5-(2-methoxyphenyl)-3-phenyl-1,3,4-oxadiazol-2-one (Example 11) are dissolved in 60 ml of dichloromethane and 17.9 g of BBr₃ are added dropwise with cooling (0–5° C.). After 24 hours stirring at ambient temperature the mixture is carefully added to 50 ml of cooled methanol and combined with dilute, aqueous HCl solution. The organic phase is separated off and washed successively with aqueous Na₂CO₃ solution (17%) and water. After the collected organic phases have been dried over Na₂SO₄ the solvent is distilled off. The remaining crude product is purified by crystallisation from n-hexane.
Yield: 5.2 g (86%), melting point: 148° C.;

b) 5-{2-[2(N,N-dimethylamino)ethyl]oxy-phenyl}-3-phenyl-1,3,4-oxadiazol-2-one 1 g of 5-(2-hydroxyphenyl)-3-phenyl-1,3,4-oxadiazol-2-one are dissolved in 10 ml of DMF and combined with 0.24 g of sodium hydride (80% in oil). The mixture is then stirred for a further 20 minutes at ambient temperature and 0.57 g of 2-N,N-dimethylaminoethylchloride-hydrochloride are added. This mixture is heated to 100° C. for 3 hours and after cooling added to water. After extraction with ethyl acetate and drying the combined organic phases over sodium sulphate the solvent is distilled off in vacuo and the residue remaining is chromatographed on silica gel (dichloromethane:methanol 95:5). The resulting free base is dissolved in acetone and converted into the hydrochloride by the addition of ethanolic HCl solution. Yield: 0.34 g, melting point: 170° C. (hydrochloride);

EXAMPLE 13

3-(2-methoxyohenyl)-5-phenyl-1H-pyrrole

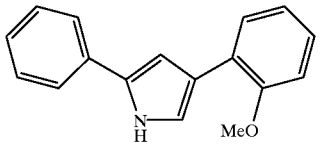

a) 3-(2-methoxyphenyl)-1-phenyl-2-propen-1-one:

To a solution of 6,4 g of NaOH in 90 ml of water and 40 ml of ethanol are added, at 10° C., 15 g of acetophenone and 17 g of 2-methoxybenzaldehyde. After 5 hours stirring at ambient temperature the mixture is diluted with water and extracted with dichloromethane. The organic phase is dried over MgSO₄ and evaporated down. 32 g of 3-(2-methoxyphenyl)-1-phenyl-2-propen-1-one remain as a colourless oil which is used in the next step without any further purification.

b) 3-(2-methoxyphenyl)-4-nitro-1-phenyl-butan-1-one:

To a solution of 32 g of 3-(2-methoxyphenyl)-1-phenyl-2-propen-1-one and 6,6 ml of nitromethane in methanol are added 3,3 g of sodium methoxide in methanol. The mixture obtained is heated to 50° C. with stirring for 2 hours and, after cooling, slowly adjusted to pH 5 by the addition of acetic acid. This solution is diluted with water and then extracted with dichloromethane. After the collected organic phases have been dried the solvent is distilled off. 34 g of 3-(2-methoxyphenyl)-4-nitro-1-phenyl-butan-1-one remain as a colourless oil which is used in the next step without any further purification.

c) 3-(2-methoxyphenyl)-5-phenyl-2,3-dihydro-1H-pyrrole:

34 g of 3-(2-methoxyphenyl)-4-nitro-1-phenyl-butan-1-one are stirred with Raney nickel in ethyl acetate for 2 days under a hydrogen atmosphere. After the catalyst has been filtered off and the solvent has been distilled off in vacuo, 24 g of 3-(2-methoxyphenyl)-5-phenyl-2,3-dihydro-1H-pyrrole are left as a colourless oil which is used in the next step without any further purification.

d) 3-(2-methoxyphenyl)-5-phenyl-1H-pyrrole:

A mixture of the remaining 24 g of 3-(2-methoxyphenyl)-5-phenyl-2,3-dihydro-1H-pyrrole and 2 g of Pd/C (30%) in 200 ml of p-cymol is refluxed for 2 hours. After the catalyst has been filtered off and the solvent has been distilled off in vacuo an oily residue is left which is purified by chromatography on silica gel (cyclohexane:ethyl acetate 9:1).
Yield: 6 g (25%), melting point: 90–93° C. (n-hexane);

EXAMPLE 14

3-{2-[2(N,N-dimethylamino)ethyl]oxy-phenyl}-5-phenyl-1H-pyrrole

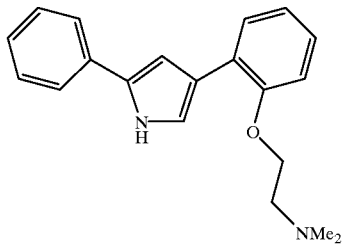

a) 3-(2-hydroxyphenyl)-5-phenyl-1H-pyrrole:

This is prepared from 3-(2-methoxyphenyl)-5-phenyl-1H-pyrrole (Example 3) analogously to Example 12 (step a). Melting point: 144–146° C.;

b) 3-{2-[2(N,N-dimethylamino)ethyl]oxy-phenyl}-5-phenyl-1H-pyrrole:

This is prepared from 3-(2-hydroxyphenyl)-5-phenyl-1H-pyrrole analogously to Example 12 (step b). Melting point: 105–108° C.;

EXAMPLE 15

1-(2-methoxyphenyl)-3-phenyl-pyrrole

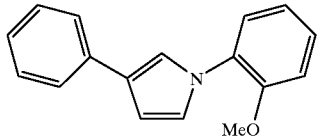

a) 2-(2-methoxyhenyl)amino-1-phenyl-ethan-1-one:

A mixture of 10 g of 2-bromoacetophenone, 5,62 ml of 2-methoxyaniline and 5,85 g of Na₂CO₃ in ethanol is stirred for 18 hours. After diluting with water it is stirred for a further 30 minutes and the mixture is filtered. After the separated solid has been washed with water and hexane 9,7 g of 2-(2-methoxyphenyl)amino-1-phenyl-ethan-1-one remain as a greenish-yellow solid. No further purification is carried out.

b) 2,3-Di(methoxycarbonyl)-1-(2-methoxyphenyl)-4-phenyl-pyrrole:

A solution of 7,4 g of 2-(2-methoxyphenyl)amino-1-phenyl-ethan-1-one and 11,3 ml of dimethyl acetylenedicarboxylate in 150 ml of toluene is refluxed for 12 hours and then the solvent is eliminated in vacuo. The residue remaining is taken up in ethyl acetate and washed with water. After the organic phase has been dried the solvent is distilled off in vacuo and the residue remaining is chromatographed on silica gel (n-hexane:ethyl acetate 80:20). 9,4 g of 2,3-di (methoxycarbonyl)-1-(2-methoxyphenyl)-4-phenyl-pyrrole are obtained as a colourless oil.

c) 2,3-Dicarboxy-1-(2-methoxyphenyl)-4-phenyl-pyrrole:

A solution of 8,4 g of 2,3-di(methoxycarbonyl)-1-(2-methoxyphenyl)-4-phenyl-pyrrole and 2.6 g of KOH in diethyleneglycol monomethylether is refluxed for 3 hours. After cooling it is poured onto water, acidified and extracted 3 times with diethylether. The combined organic phases are washed with water, dried and evaporated down. The crude product is crystallised from diethylether. 4,8 g of 2,3-dicarboxy-1-(2-methoxyphenyl)-4-phenyl-pyrrole are obtained.

d) 1-(2-methoxyphenyl)-3-phenyl-pyrrole:

4.8 g of 2,3-dicarboxy-1-(2-methoxyphenyl)-4-phenyl-pyrrole and 2 g of Cu powder are heated for 2 hours to about 200° C. in 50 ml of quinoline. After cooling the Cu powder is filtered off. The filtrate is diluted with water, acidified with dilute aqueous HCl solution and extracted with ethyl acetate. The organic phase is washed successively with dilute, aqueous HCl solution, NaHCO₃ solution and water and then dried. After the solvent has been distilled off in vacuo the remaining product is purified by chromatography on silica gel (cyclohexane:ethyl acetate 95:5). 1.6 g of 1-(2-methoxyphenyl)-3-phenyl-pyrrole are obtained in the form of a colourless oil.

EXAMPLE 16

1-{2-[2(N,N-dimethylamino)ethyl]oxy-phenyl}-3-phenyl-pyrrole

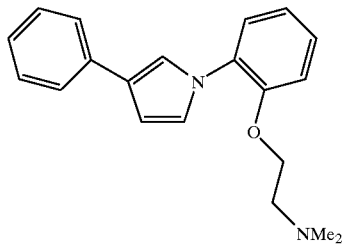

a) 1-(2-hydroxyphenyl)-3-phenyl-pyrrole:

This is prepared from 1-(2-methoxyphenyl)-3-phenyl-pyrrole (Example 15) analogously to Example 12 (step a). Colourless oil.

b) 1-(2-[2(N,N-dimethylamino)ethyl]oxy-phenyl}-3-phenyl-pyrrole:

This is prepared from 1-(2-hydroxyphenyl)-3-phenyl-pyrrole analogously to Example 12 (step b). Melting point: 116–121° C. (hydrochloride);

EXAMPLE 17

4-(2-methoxyphenyl)-1-phenyl-pyrazole

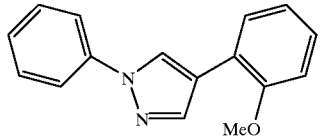

a) 1-methoxy-2-(2-methylsulphanyl-vinyl)-benzene:

2.6 ml of a 1.6 M butyllithium solution in tetrahydrofuran are slowly added dropwise at 0° C. to a solution of 1.5 g of methylmercaptomethyl-triphenyl-phosphonium chloride in anhydrous tetrahydrofuran. After 1 hour, 5.7 g of 2-methoxybenzaldehyde in 50 ml of tetrahydrofuran are added and the resulting mixture is stirred for a further 12 hours at ambient temperature. The solvent is distilled off in vacuo and the residue remaining is taken up in diethylether. After extraction with dilute, aqueous HCl solution, aqueous Na₂CO₃ solution (17%) and washing with water, the collected organic phases are dried and the solvent is distilled off in vacuo. Chromatography on silica gel (cyclohexane:ethyl acetate 90:10) yields 5.5 g of 1-methoxy-2-(2-methylsulphanyl-vinyl)-benzene.

b) 2-(2-methoxyphenyl)-3-methylsulphanyl-propenal:

A solution of 5.5 g of 1-methoxy-2-(2-methylsulphanyl-vinyl)-benzene in 15 ml of dimethylformamide is heated to 80° C. with 4.7 g of POCl₃ for 2 hours with stirring. After cooling diethylether and water are carefully added and the mixture obtained is adjusted to pH 9 with aqueous NaOH solution (10%). The organic phase is separated off and after drying the solvent is eliminated in vacuo. Chromatography on silica gel (cyclohexane:ethyl acetate 70:30) yields 2.5 g of 2-(2-methoxyphenyl)-3-methylsulphanyl-propenal.

c) 4-(2-methoxyphenyl)-1-phenyl-pyrazole:

A solution of 2,4 g of 2-(2-methoxyphenyl)-3-methylsulphanyl-propenal in anhydrous dioxane is refluxed with 1,3 g of phenylhydrazine over 24 hours. The solvent is distilled off in vacuo and the residue is taken up in diethylether and dilute, aqueous HCl solution. The organic phase is dried and evaporated down and the oily residue is purified on silica gel (cyclohexane:ethyl acetate 95:5).

Yield: 0.85 g, melting point: 60–68° C. (n-hexane);

EXAMPLE 18

4-{2-[2(N,N-dimethylamino)ethyl]oxy-phenyl}-1-phenyl-pyrazole

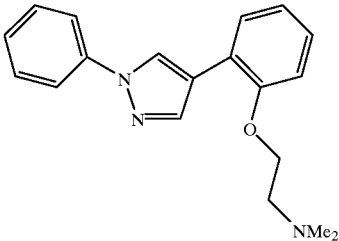

a) 4-(2-hydroxyphenyl)-1-phenyl-pyrazole:

This is prepared from 4-(2-methoxyphenyl)-1-phenyl-pyrazole (Example 17) analogously to Example 12 (step a). Melting point: 205–208° C. (diethylether);

b) 4-{2-[2(N,N-dimethylamino)ethyl]oxy-phenyl}-1-phenyl-pyrazole:

This is prepared from 4-(2-hydroxyphenyl)-1-phenyl-pyrazole analogously to Example 12 (step b). Melting point: 150° C. (hydrochloride);

EXAMPLE 19

3-{2-[2(N,N-dimethylamino)ethyl]oxy-phenyl}-5-phenyl-imidazolidin-2,4-dione

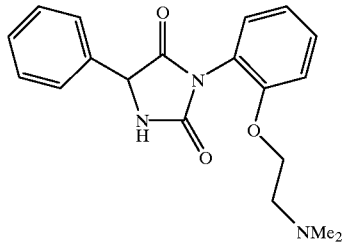

a) 1-[2(N,N-dimethylamino)ethyl]oxy-2-nitro-benzene:

23 g of 2-N,N-dimethylaminoethylchloride-hydrochloride are added to 24 g of nitrophenol and 72 g of $K_2CO_3$ in anhydrous acetone with stirring. This mixture is refluxed for 7 hours. For working up it is cooled and dilute, aqueous HCl solution is added slowly. After extraction with diethylether the aqueous phase is adjusted to pH 9 and extracted with ethyl acetate. Drying the ethyl acetate phase and distilling off the solvent in vacuo yields 11 g of 1-[2(N,N-dimethylamino)ethyl]oxy-2-nitro-benzene as a yellow oil, which is used in the next phase without further purification.

b) 2-[2(N,N-dimethylamino)ethyl]oxy-aniline:

11 g of 1-[2(N,N-dimethylamino)ethyl]oxy-2-nitro-benzene are stirred in 200 ml of ethanol at ambient temperature over a period of 6 hours in the presence of 0.5 g of Pd/C (10%) under a hydrogen atmosphere. After filtration and distilling off the solvent in vacuo, 8.5 g of a colourless oil remain, which is used in the next step without further purification.

c) 1-[2(N,N-dimethylamino)ethyl]oxy-2-isocyanate-benzene:

To 8 g of 2-[2(N,N-dimethylamino)ethyl]oxy-aniline in 80 ml of dioxane are added 5,5 ml of trichloromethyl-chloroformate (diphosgene). After 2 hours stirring at 60° C. the solvent is distilled off in vacuo. 9 g of crude product remain, which is used in the next step without further purification.

d) 3-{2-[2(N,N-dimethylamino)ethyl]oxy-phenyl}-5-phenyl-imidazolidin-2,4-dione

To a solution of 6.6 g of phenylglycine and 2.9 g of potassium hydroxide in water (about 20 ml) are slowly added 10 g of the isocyanate generated according to step (c). The mixture is stirred for 12 hours at ambient temperature, filtered and acidified with dilute, aqueous HCl solution (about pH 2). The precipitate formed is separated off and refluxed in a mixture of 8% aqueous HCl solution in ethanol (150 ml). After 6 hours this is slowly cooled and made alkaline with aqueous $Na_2CO_3$ solution (17%). The precipitate obtained is recrystallised from ethyl acetate. 2,4 g of the title compound are obtained.

EXAMPLE 20

1-{2-[2(N,N-dimethylamino)ethyl]oxy-phenyl}-4-phenyl-1,3-dihydro-imidazole-2-one

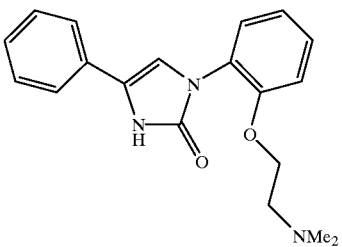

To a solution of 2.4 g of 3-{2-[2(N,N-dimethylamino)ethyl]oxy-phenyl}-5-phenyl-imidazolidin-2,4-dione (cf. Example 9) in 50 ml of anhydrous tetrahydrofuran are slowly added 14,1 ml of RED-Al. This mixture is stirred for 12 hours at ambient temperature, cooled and combined with aqueous HCl solution (10%). After extraction with dichloromethane, drying the collected organic phases and distilling off the solvent in vacuo, the residue is purified by chromatography on silica gel (dichloromethane:methanol 90:10). The resulting oil is converted into the hydrochloride using ethereal HCl solution.

Yield: 0.4 g; melting point: 220–223° C. (hydrochloride).

EXAMPLE 21

5-{2-[2(N,N-dimethylamino)ethyl]oxy-phenyl}-3-phenyl-imidazolidin-2,4-dione

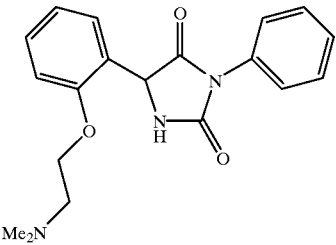

a) 2-[2(N,N-dimethylamino)ethyl]oxy-benzaldehyde:

To 26 ml of 2-hydroxybenzaldehyde and 90 g of $K_2CO_3$ in anhydrous acetone are added 58 g of 2-N,N-dimethylaminoethylchloride-hydrochloride with stirring. This mixture is refluxed for 7 hours. For working up, it is cooled and dilute, aqueous HCl solution (5%) is slowly added. After extraction with diethylether the aqueousphase is adjusted to pH 9 and extracted with ethyl acetate. Drying the ethyl acetate phase and distilling off the solvent in vacuo yields 11 g of 2-[2(N,N-dimethylamino)ethyl]oxy-benzaldehyde as a yellow oil, which is used in the next phase without further purification.

b) 2-amino-2-{[2(N,N-dimethylamino)ethyl]oxy-phenyl}-acetic acid:

29 g of 2-[2(N,N-dimethylamino)ethyl]oxy-benzaldehyde-hydrochloride and 73 g of ammonium carbonate are taken up in 500 ml of ethanol (50%). This mixture is combined with 16,4 g of potassium cyanide. This mixture is heated to 60° C. and stirred at constant temperature for 8 hours. After cooling it is acidified to pH 2 with aqueous HCl. The ethanol is carefully distilled off in vacuo and the aqueous phase is made alkaline (pH 10) with aqueous NaOH solution (10%). After extraction with dichloromethane and distilling off the organic solvent, 10 g of a white precipitate remain, which is refluxed in aqueous HBr solution (48%) for 14 hours. The product (5 g) is obtained in the form of a white solid (melting point: 195–196° C.) after evaporation and crystallisation from methanol:acetic acid 50:1.

c) 5-{2-[2(N,N-dimethylamino)ethyl]oxy-phenyl}-3-phenyl-imidazolidine-2,4-dione 1.4 ml of phenyl isocyanate are slowly added to a solution of 4 g of 2-amino-2-{[2(N,N-dimethylamino)ethyl]oxy-phenyl}-acetic acid and 1.65 g of potassium hydroxide in water (about 20 ml). The mixture is stirred for 12 hours at ambient temperature, filtered, acidified with aqueous HCl solution (10%) (about pH 2) and refluxed. After 6 hours it is slowly cooled and made alkaline with aqueous $Na_2CO_3$ solution (10%). The precipitate obtained is recrystallised from ethyl acetate. 3 g of the title compound are obtained in the form of a white solid (melting point: 120–124° C.).

EXAMPLE 22

4-{2-[2(N,N-dimethylamino)ethyl]oxy-phenyl}-1-phenyl-1,3-dihydro-imidazol-2-one

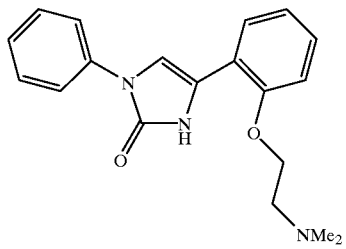

8,8 ml of RED-Al are slowly added to a solution of 1.5 g of 5-{2-[2(N,N-dimethylamino)ethyl]oxy-phenyl}-3-phenyl-imidazolidin-2,4-dione (cf. Example 11) in 30 ml of anhydrous tetrahydrofuran. This mixture is stirred for 12 hours at ambient temperature, cooled and combined with aqueous HCl solution (10%). After extraction with dichloromethane, drying the collected organic phases and distilling off the solvent in vacuo, the residue is purified by chromatography on silica gel (dichloromethane:methanol 90:10). The resulting oil is converted into the hydrochloride using ethereal HCl solution.

Yield: 0.15 g; melting point: 215–218° C. (hydrochloride).

d) 5-(2-hydroxyphenyl)-2-phenyl-1,3-oxazole 0.55 g of 5-(2-benzyloxyphenyl)-2-phenyl-1,3-oxazole according to step (c) are hydrogenated in 30 ml of tetrahydrofuran in the presence of 0.1 g of Pd/C catalyst (10W) at about 60° C. (5.7 bar). After the catalyst has been separated off the solvent is distilled off in vacuo and the residue remaining is chromatographed on silica gel (dioxane:hexane 3:5).

Yield: 0.38 g (95%);

e) 5-{2-[2(N,N-dimethylamino)ethyl]oxy-phenyl}-2-phenyl-1,3-oxazole 0.38 g of 5-(2-hydroxyphenyl)-2-phenyl-1,3-oxazole are dissolved in 6 ml of DMF and at 0° C. 1,6 ml of a 1 molar solution of lithium hexamethyldisilazide in hexane is slowly added. After 15 minutes stirring at ambient temperature, a mixture of 0.69 g of 2-N,N-dimethylaminoethylchloride-hydrochloride and 4,8 mmol of lithium hexamethyldisilazane in 8 ml of DMF which has previously been stirred for 30 minutes is added dropwise. This mixture is refluxed for 6 hours and then the solvent is eliminated in vacuo. The residue is taken up in water and extracted twice with ethyl acetate. The organic phase is dried over sodium sulphate, evaporated down in vacua and chromatographed on silica gel (ethyl acetate:isopropanol 70:30) After the purification the title compound is converted into the hydrochloride.

Yield: 0.18 g (33%), melting point (hydrochloride): 246–247° C.

The compounds of general formula (I) wherein $R^2$, $R^3$, $R^4$ and $R^5$=hydrogen listed in Table 1 may also be prepared according to the processes described hereinbefore or by analogous processes:

TABLE 1

(I)

| Ex. | | —X— | -R¹ | melting point [° C.] | Chemical name |
|---|---|---|---|---|---|
| 23 | Ph, N, N–N, Me (triazole) | —O— | NMe | 118–120 d | 5-{2-[2(N,N-dimethylamino)-ethyl]oxy-phenyl}-1-methyl-3-phenyl-1,2,4-triazole |
| 24 | Ph, H, N (pyrrole) | —O— | NMe | 237 a | 2-{2-[2(N,N-dimethylamino)-ethyl]oxy-phenyl}-5-phenyl-pyrrole |

TABLE 1-continued

| Ex. | A (aryl group) | —X— | -R¹ | melting point [°C.] | Chemical name |
|---|---|---|---|---|---|
| 25 | Ph-imidazole (2-methyl, 4-phenyl, NH) | —O— | ethyl-NMe₂ | 176–177 ᵉ | 2-{2-[2-(N,N-dimethylamino)-ethyl]-oxy-phenyl}-4-phenyl-imidazole |
| 26 | Ph-imidazole (2-methyl, 4-phenyl, N-Me) | —O— | ethyl-NMe₂ | 141–143 ᵉ | 2-{2-[2-(N,N-dimethylamino)-ethyl]oxy-phenyl}-1-methyl-4-phenyl-imidazole |
| 27 | Ph-imidazole (2-phenyl, 4-methyl, N-Me) | —O— | ethyl-NMe₂ | 177–178 ᵇ | 4-{2-[2-(N,N-(dimethylamino)-ethyl]oxy-phenyl}-1-methyl-2-phenyl-imidazole |
| 28 | Ph-pyrazole (3-methyl, 5-OH, 1-phenyl) | —O— | ethyl-NMe₂ | 185–188 ᵃ | 3-{2-[2-(N,N-dimethylamino)-ethyl]oxy-phenyl}-5-hydroxy-1-phenyl-pyrazole |
| 29 | Ph-oxazole (2-methyl, 5-phenyl) | —O— | ethyl-NMe₂ | 178–180 ᵃ | 2-{2-[2-(N,N-dimethylamino)-ethyl]oxy-phenyl}-5-phenyl-oxazole |
| 30 | Ph-oxazole (2-methyl, 4-methyl, 5-phenyl) | —O— | ethyl-NMe₂ | 155–157 ᵇ | 2-{2-[2-(N,N-dimethylamino)-ethyl]oxy-phenyl}-4-methyl-5-phenyl-oxazole |
| 31 | Ph-pyrazole (3-phenyl, 5-methyl, N-CH₂CH₂NMe₂) | —O— | —H | 215–217 ᵃ | 1-[2(N,N-dimethylamino)ethyl]-5-(2-hydroxyphenyl)-3-phenyl-pyrazole |
| 32 | Ph-pyrazole (3-phenyl, 5-methyl, NH) | —O— | ethyl-NMe₂ | 130–133 ᶜ | 5-{2-[2-(N,N-dimethylamino)-ethyl]oxy-phenyl}-3-phenyl-pyrazole |

TABLE 1-continued (I)

| Ex. | [A-aryl group] | —X— | -R¹ | melting point [° C.] | Chemical name |
|---|---|---|---|---|---|
| 33 | Ph, 3-methyl-5-phenyl-1-(2-NMe₂-ethyl)-pyrazole | —O— | ~NMe (CH₂CH₂NMe₂) | 253–254 [b] | 1-[2(N,N-dimethylamino)ethyl]-5-{2-[2-(N,N-dimethylamino)-ethyl]oxy-phenyl}-3-phenyl-pyrazole |
| 34 | Ph, 3-methyl-1-methyl-5-phenyl-pyrazole | —O— | ~NMe | 218–220 [b] | 3-{2-[2(N,N-dimethylamino)-ethyl]oxy-phenyl}-1-methyl-5-phenyl-pyrazole |
| 35 | Ph, 5-methyl-1-methyl-3-phenyl-pyrazole | —O— | ~NMe | 113–115 [b] | 5-{2-[2-N,N-dimethylamino)-ethyl]oxy-phenyl}-1-methyl-3-phenyl-pyrazole |
| 36 | Ph, 3-phenyl-5-methyl-isoxazole | —O— | ~NMe | 182–183 [a] | 5-{2-[2(N,N-dimethylamino)-ethyl]oxy-phenyl}-3-phenyl-isoxazole |
| 37 | Ph, 5-phenyl-3-methyl-isoxazole | —O— | ~NMe | 172–175 [a] | 3-{2-[2(N,N-dimethylamino)-ethyl]oxy-phenyl}-5-phenyl-isoxazole |
| 38 | Ph, 1-phenyl-pyrrole | —O— | -methyl | 93–95 | 3-(2-methoxyphenyl)-1-phenyl-pyrrole |
| 39 | Ph, 1-phenyl-pyrrole | —O— | —H | 72–74 | 3-(2-hydroxyphenyl)-1-phenyl-pyrrole |
| 40 | Ph, 1-phenyl-pyrrole | —O— | ~NMe | 217–219 [a] | 3-{2-[2(N,N-dimethylamino)ethyl]oxy-phenyl}-1-phenyl-pyrrole |
| 41 | Ph, 4-phenyl-1H-pyrrole | —O— | ~NMe | 177–179 [a] | 2-{2-[2(N,N-dimethylamino)ethyl]oxy-phenyl}-4-phenyl-1H-pyrrole |
| 42 | Ph, 4-phenyl-1-methyl-pyrazole | —O— | —H | — | 1-(2-hydroxyphenyl)-4-phenyl-pyrazole |

TABLE 1-continued

| Ex. | A | —X— | -R¹ | melting point [° C.] | Chemical name |
|---|---|---|---|---|---|
| 43 | Ph-pyrazole-N- | —O— | -methyl | — | 1-(2-methoxyphenyl)-4-phenyl-pyrazole |
| 44 | Ph-pyrazole-N- | —O— | CH₂CH₂CH₂NMe | — | 1-{2-[2(N,N-dimethylamino)ethyl]oxy-phenyl}-4-phenyl-pyrazole |
| 45 | Ph-oxadiazolone-N- | —O— | -methyl | 129–131 | 3-(2-methoxyphenyl)-5-phenyl-1,3,4-oxadiazol-2-one |
| 46 | Ph-oxadiazolone-N- | —O— | —H | 135 | 3-(2-hydroxyphenyl)-5-phenyl-1,3,4-oxadiazol-2-one |
| 47 | Ph-oxadiazolone-N- | —O— | CH₂CH₂CH₂NMe | — | 3-{2-[2(N,N-dimethylamino)-ethyl]oxy-phenyl}-5-phenyl-1,3,4-oxadiazol-2-one |
| 48 | Ph-oxazolinone-N- | —O— | —H | 208–209 | 5-(2-hydroxyphenyl)-3-phenyl-oxazolin-2-one |
| 49 | Ph-oxazolinone-N- | —O— | -methyl | 125–127 | 5-(2-methoxyphenyl)-3-phenyl-oxazolin-2-one |
| 50 | Ph-oxazolinone-N- | —O— | CH₂CH₂CH₂NMe | 205 [a] | 5-{2-[2(N,N-dimethylamino)ethyl]oxy-phenyl}-3-phenyl-oxazolin-2-one |
| 51 | Ph-oxazolinone-N- | —O— | —H | 192–193 | 3-(2-hydroxyphenyl)-5-phenyl-oxazolin-2-one |

TABLE 1-continued (I)

| Ex. | A (with R4, R5, Ph) | —X— | -R¹ | melting point [° C.] | Chemical name |
|---|---|---|---|---|---|
| 52 | Ph-oxazolin (N-Me) | —O— | -methyl | 156–158 | 3-(2-methoxyphenyl)-5-phenyl-oxazolin-2-one |
| 53 | Ph-oxazolin (N-Me) | —O— | ~~~NMe (propyl-NMe) | 180 a | 3-{2-[2(N,N-dimethylamino)ethyl]oxy-phenyl}5-phenyl-oxazolin-2-one |
| 54 | Ph-imidazol (NH, N-Me) | —O— | —H | 253–255 | 1-(2-hydroxyphenyl)-4-phenyl-1,3-dihydro-imidazol-2-one | ax HCl;
bx 2HCl;
cx 1,5 HCl;
dx 1,5 oxalic acid;
ex 2 oxalic acid.

Surprisingly, it has been found that the compounds according to the invention have an affinity for or an activity on various types of receptor and exhibit a neuroprotective effect.

Tests in vitro and in viva have shown that the cell damage and loss of function occurring in the brain as a result of hypoglycaemia, hypoxia, anoxia, global and focal ischaemia, cranial brain trauma, brain oedema and intercranial pressure are due in some measure to an increased synaptic activity and hence increased release of transmitters. Apart from glutamate, histamine and serotonin are of particular importance as neurotransmitters. Moreover, the concentrations of calcium and sodium ions in particular are changed.

It is known that after systemic administration of glutamate neurones are destroyed in mouse brains (S. M. Rothman and T. W. Olney, Trends in Neurosciences 10 (1987) 299). This finding leads one to conclude, inter alia, that glutamate plays a part in neurodegenerative diseases (R.Schwarcz and B. Meldrum, The Lancet 11 (1985) 140). Moreover, substances such as for example quisqualic acid, cainic acid, ibotenic acid, glutamic acid, N-methyl-D-aspartic acid (NMDA) and α-amino-3-hydroxy-5-methyl-4-isooxazol-propionic acid (AMPA) are known as exogenous or endogenous neurotoxins. Brain lesions which may be induced by such substances are comparable with those which occur in conjunction with epilepsy and other neurodegenerative disoders—such as, for example, Huntington's disease and Alzhiemer's disease. Substances and ions which inhibit the activity of the glutamate receptor and the ion channel connected to this receptor—such as e.g. competitive and non-competitive antagonists of excitatory amino acids—protect brain cells from hypoxic or ischaemic damage. These findings show that the glutamate receptors play an important part in mediating ischaemic damage.

The activity at the AMPA receptor was demonstrated by electrophysiology on neuronal cells (patch-clamp method) (M. L. Mayer, L. Vyklicky and G. L. Westbrook, J. Physiol. 415 (1989) 329–350).

The testing was carried out at a test concentration of 100 $\mu$M.

TABLE 2

Inhibition of the cainate-induced signal at the AMPA receptor

| Example | AMPA Inh. [%] |
|---|---|
| 1 | 56 |
| 2 | 96 |
| 3 | 74 |
| 5 | 76 |
| 7 | 39 |
| 8 | 77 |
| 10 | 98 |
| 17 | 53 |

The affinity to the "$Na^+$ channel site 2" binding site was demonstrated as described by G. B. Brown (J. Neurosci. 6

(1986) 2064). The testing was typically carried out at a test concentration of 10 μM.

TABLE 3

| Example | Ki [μm] |
|---------|---------|
| 3 | 3.7 |
| 5 | 0.7 |
| 7 | 1.2 |
| 8 | 4.6 |
| 9 | 1.8 |
| 10 | 0.99 |
| 12 | 0.99 |
| 13 | 1.1 |
| 17 | 0.39 |
| 19 | 0.55 |
| 20 | 0.36 |
| 21 | 0.71 |
| 22 | 1.3 |
| 23 | 1.4 |
| 24 | 0.46 |
| 25 | 1.3 |

The results described above show that the compounds of general formula (I) can be used in the treatment of neurodegenerative diseases and cerebral ischaemia of various origins. These include, for example: Status epilepticus, hypoglycaemia, hypoxia, anoxia, brain trauma, brain oedema, amyotropic lateral sclerosis, Huntington's disease, Alzheimer's disease, hypotonia, cardiac infarction, brain pressure (elevated intracranial pressure), ischaemic and haemorrhagic stroke, global cerebral ischaemia with heart stoppage, diabetic polyneuropathy, tinnitus, perinatal asphyxia, psychosis, schizophrenia, depression and Parkinson's disease.

The compounds of general formula (I) may be used on their own or in conjunction with other active substances according to the invention, optionally also in conjunction with other pharmacologically active substances. Suitable preparations include for example tablets, capsules, suppositories, solutions,—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, optionally organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof. Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by parenteral route, particularly by intravenous infusion. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above. For parenteral use, solutions of the active substances with suitable liquid carriers may be used. The dosage for intravenous use is from 1–1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

Moreover, the compounds of general formula I or the acid addition salts thereof may also be combined with other types of active substance.

The Examples which follow illustrate the present invention without restricting its scope:

Examples of Pharmaceutical Formulations

| A) | Tablets | per tablet |
|---|---|---|
| | active substance | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance | 80 mg |
| | lactose | 55 mg |
| | corn starch | 190 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

What is claimed is:

1. A compound of the formula (I)

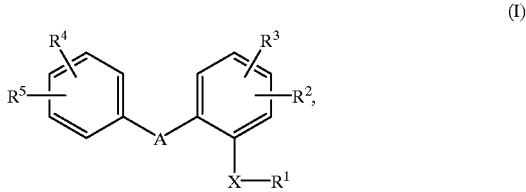

wherein:

the moiety of the formula

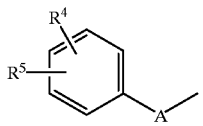

denotes a group selected from the class consisting of:

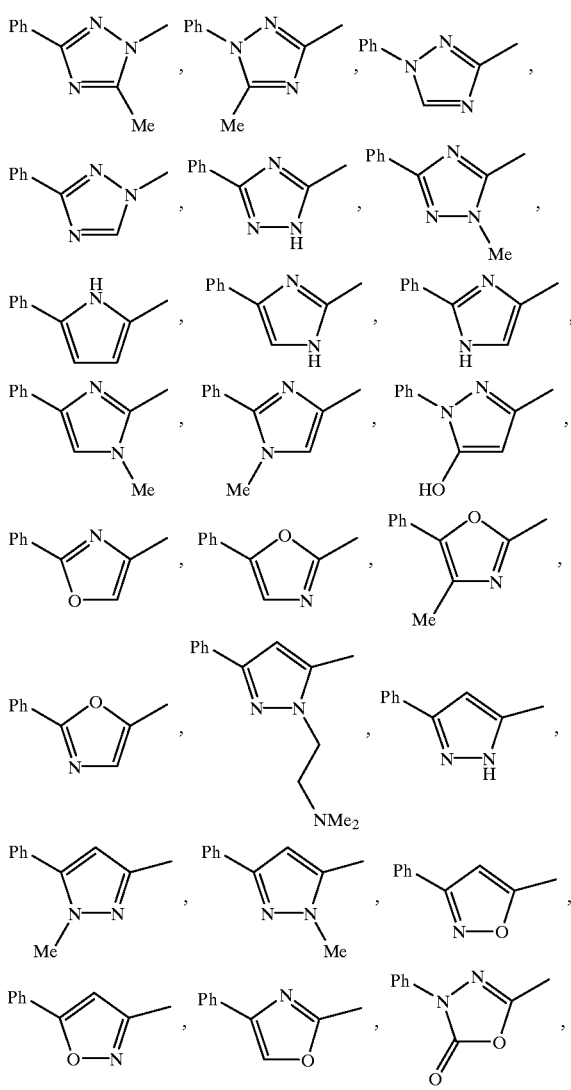

-continued

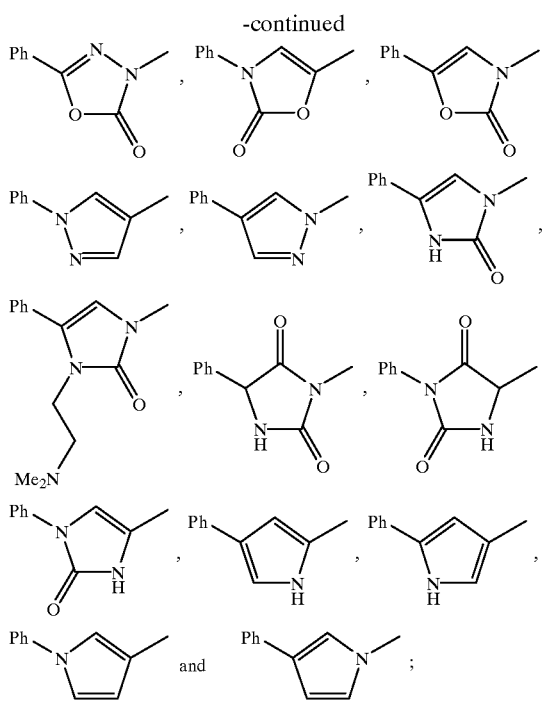

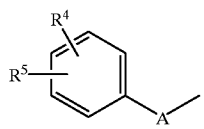 and 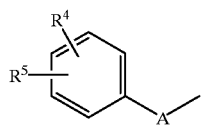;

X denotes oxygen;
R¹ denotes an ethyl or propyl group which is substituted by —NPR⁶R⁷;
R² and R³ denote hydrogen;
R⁴ and R⁵ denote hydrogen;
R⁶ denotes hydrogen, methyl, ethyl, propyl or butyl; and,
R⁷ denotes hydrogen, methyl, ethyl, propyl or butyl;
or a pharmaceutically acceptable salt thereof.

2. A compound of the formula (I), according to claim 1, wherein: the moiety of the formula

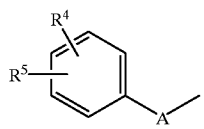

is a group selected from the class consisting of:

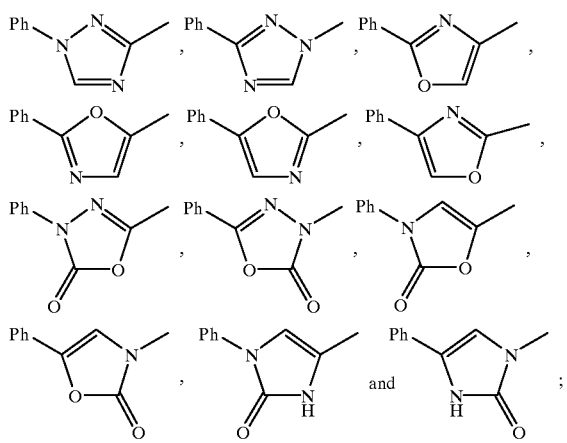

X denotes oxygen;

R¹ denotes an ethyl or propyl group which is substituted by —NR⁶R⁷;
R² and R³ denote hydrogen;
R⁴ and R⁵ denote hydrogen;
R⁶ denotes hydrogen, methyl, ethyl, propyl or butyl; and,
R⁷ denotes hydrogen, methyl, ethyl, propyl or butyl;
or a pharmaceutically acceptable salt thereof.

3. A compound of the formula (I), according to claim 1, wherein:
the moiety of the formula

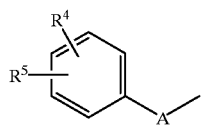

is selected from the class consisting of:

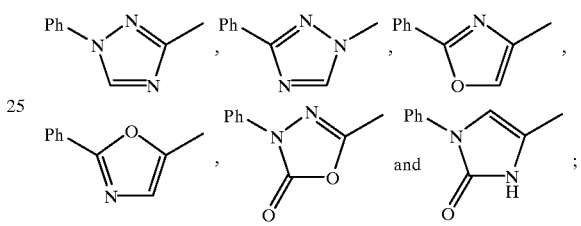

X denotes oxygen;
R¹ denotes —CH₂—CH₂—NR⁶R⁷;
R² and R³ denote hydrogen;
R⁴ and R⁵ denote hydrogen;
R⁶ denotes methyl; and,
R⁷ denotes methyl;
or a pharmaceutically acceptable salt thereof.

4. A method for treating or inhibiting damage to the brain due to hypoxia or ischemia which comprises adminstering to a host suffering from hypoxia or cerebral ischemia a therapeutic amount of a compound of the formula (I)

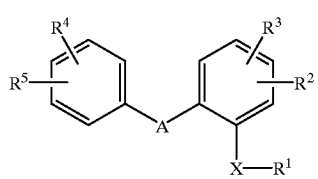

(I)

wherein:
A denotes a 5-membered saturated or unsaturated heterocycle other than 1,2,4-oxadiazole, which may contain 1, 2 or 3 heteroatoms selected from the group consisting of oxygen, nitrogen and sulphur and is optionally mono- or polysubstituted by —OR⁸, =O or C₁–C₆-alkyl, whilst the C₁–C₆-alkyl group may in turn be substituted by halogen, hydroxy or —NR⁶R⁷;
X denotes oxygen, sulphur or NR⁶;
R¹ denotes a C₁–C₁₀-alkyl, C₂–C₁₀-alkenyl or C₂–C₁₀-alkynyl group which may optionally be mono- or polysubstituted by =O, —CN, —CHO, C₆–C₁₀-aryl, —COOR⁸, —CONHSO₂R⁸, —CONR⁶R⁷, —CH=NOR⁸, —COR⁸, —NR⁶R⁷, —NHCOR⁸, —NHCONR⁶R⁷, —NHCOOR⁸, —OR⁸, —OCOR⁸, —OCOOR$^8$, —OCONR$^6$R$^7$, —SR$^8$, —SOR$^8$, —SO$_2$R$^8$, —SO$_3$H, —SO$_2$NR$^6$R$^7$, halogen or by an N-oxide of the formula —NOR$^6$R$^7$;

R$^2$ and R$^3$ which may be identical or different, denote hydrogen, mercapto, —NR$^6$R$^7$, halogen, nitro, CF$_3$, CN, —OR$^8$, C$_1$–C$_{10}$-alkyl, C$_2$–C$_{10}$-alkenyl or C$_2$–C$_{10}$-alkynyl; or, R$^2$ and R$^3$ which may be identical or different, denote C$_6$–C$_{10}$-aryl, aryl-C$_1$–C$_6$-alkyl, C$_6$–C$_{10}$-aryloxy;

R$^4$ and R$^5$ which may be identical or different, denote hydrogen, mercapto, —NR$^6$R$^7$, halogen, nitro, CF$_3$, CN, —OR$^8$, C$_1$–C$_{10}$-alkyl, C$_2$–C$_{10}$-alkenyl or C$_2$–C$_{10}$-alkynyl; or, R$^4$ and R$^5$ which may be identical or different, denote C$_6$–C$_{10}$-aryl, aryl-C$_1$–C$_6$-alkyl or C$_6$–C$_{10}$-aryloxy;

R$^6$ denotes hydrogen, C$_3$–C$_6$-cycloalkyl, C$_1$–C$_{10}$-alkyl, C$_2$–C$_{10}$-alkenyl or C$_2$–C$_{10}$-alkynyl, each of which may be mono- or polysubstituted by phenyl, benzyl or —OR$^8$; or, R$^6$ denotes C$_6$–C$_{10}$-aryl, which may optionally be substituted by halogen, —OR$^8$, C$_1$–C$_4$-alkyl, —SO$_3$H or —COOR$^8$;

R$^7$ denotes hydrogen, C$_3$–C$_6$-cycloalkyl, C$_1$–C$_{10}$-alkyl, C$_2$–C$_{10}$-alkenyl or C$_2$–C$_{10}$-alkynyl, each of which may be mono- or polysubstituted by phenyl, benzyl or —OR$^8$; or, R$^7$ denotes C$_6$–C$_{10}$-aryl, which may optionally be substituted by halogen, —OR$^8$, C$_1$–C$_4$-alkyl, —SO$_3$H or —COOR$^8$; or, R$^6$ and R$^7$ together with the nitrogen atom form a saturated or unsaturated 5- or 6-membered ring, which may contain nitrogen, oxygen or sulphur as further heteroatoms, whilst the heterocycle may be substituted by a branched or unbranched alkyl group having 1 to 4 carbon atoms, by phenyl or by benzyl; and, R$^8$ denotes hydrogen, C$_1$–C$_4$-alkyl, C$_2$–C$_4$-alkenyl, C$_2$–C$_4$-alkynyl, a benzyl or phenyl group which is optionally mono- or polysubstituted by OH, chlorine, bromine or OCH$_3$;

or a pharmaceutically acceptable salt thereof.

* * * * *